(12) United States Patent
Shelton, IV et al.

(10) Patent No.: US 12,243,629 B2
(45) Date of Patent: Mar. 4, 2025

(54) CAPACITY TO ADJUST PATIENT CONSENT

(71) Applicant: Cilag GmbH International, Zug (CH)

(72) Inventors: Frederick E. Shelton, IV, Hillsboro, OH (US); Kevin M Fiebig, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 142 days.

(21) Appl. No.: 17/958,236

(22) Filed: Sep. 30, 2022

(65) Prior Publication Data
US 2024/0112770 A1 Apr. 4, 2024

(51) Int. Cl.
*G16H 10/60* (2018.01)
*G16H 50/30* (2018.01)

(52) U.S. Cl.
CPC .............. *G16H 10/60* (2018.01); *G16H 50/30* (2018.01)

(58) Field of Classification Search
CPC ................................ G16H 10/60; G16H 50/30
See application file for complete search history.

(56) References Cited

U.S. PATENT DOCUMENTS

| | | | | |
|---|---|---|---|---|
| 6,171,112 B1 * | 1/2001 | Clark | ..................... | G16H 40/20 434/362 |
| 6,941,271 B1 | 9/2005 | Soong | | |
| 7,308,412 B2 * | 12/2007 | Rakshit | .................. | G09B 19/00 434/350 |
| 7,860,793 B2 * | 12/2010 | Karkanias | ............ | G06Q 20/105 705/41 |
| 9,298,766 B2 * | 3/2016 | Kozloski | .................. | G06N 5/04 |
| 9,471,623 B2 * | 10/2016 | Kozloski | ............... | G06F 40/205 |
| 9,569,593 B2 * | 2/2017 | Casella dos Santos | ..................... | G16H 15/00 |
| 9,569,594 B2 * | 2/2017 | Casella dos Santos | ..................... | G16Z 99/00 |
| 9,785,753 B2 * | 10/2017 | Casella dos Santos | ..................... | G10L 15/183 |
| 9,790,557 B2 * | 10/2017 | Blelloch | ................ | G16H 50/30 |
| 9,875,592 B1 * | 1/2018 | Erickson | ................ | G06V 20/13 |
| 10,199,124 B2 * | 2/2019 | Casella dos Santos | ..................... | G10L 15/183 |

(Continued)

FOREIGN PATENT DOCUMENTS

WO 2022103404 A1 5/2022

OTHER PUBLICATIONS

Yu, Elsevier, 2014, pp. 1434-1445.*

*Primary Examiner* — Michael I Ezewoko
(74) *Attorney, Agent, or Firm* — Condo Roccia Koptiw LLP

(57) ABSTRACT

A consent management system may receive a request to modify consent data associated with a patient. The system may obtain patient capacity information associated with the patient and may determine whether to allow the patient to modify the consent data based on the obtained patient capacity information. The patient capacity information may indicate patient cognitive capacity, patient emotional capacity and/or the like. A response to the consent modification request may be generated based on the determining. For example, based on a determination that the obtained patient capacity information indicates that patient lacks the capacity to modify the consent data, the response may indicate a rejection of the request (e.g., may indicate that the consent data may not be modified). Based on a determination that the obtained patient capacity information indicates that patient possesses the capacity to modify the consent data, the response may indicate an approval of the request.

17 Claims, 12 Drawing Sheets

(56) References Cited

U.S. PATENT DOCUMENTS

| | | | |
|---|---|---|---|
| 10,304,062 B1* | 5/2019 | Hines | G06Q 30/018 |
| 10,325,079 B1* | 6/2019 | Vukich | G06F 21/121 |
| 10,348,505 B1* | 7/2019 | Crawforth | H04L 9/3236 |
| 10,355,865 B1* | 7/2019 | Crawforth | H04L 65/75 |
| 10,460,078 B2* | 10/2019 | Turner, Jr. | H04L 67/04 |
| 10,490,304 B2* | 11/2019 | Shah | G06Q 50/01 |
| 10,560,272 B2* | 2/2020 | Yang | G16H 10/60 |
| 10,592,503 B2* | 3/2020 | Kozloski | G06F 16/24578 |
| 10,628,833 B2* | 4/2020 | Hines | G06F 21/602 |
| 10,755,700 B2* | 8/2020 | Lewis | G16H 40/67 |
| 10,795,975 B2* | 10/2020 | Vukich | H04L 9/3297 |
| 10,811,124 B2* | 10/2020 | Shah | G06Q 50/01 |
| 10,853,456 B1* | 12/2020 | Crawforth | H04L 9/14 |
| 10,867,299 B2* | 12/2020 | Cheng | G06Q 20/02 |
| 10,878,939 B2* | 12/2020 | Sadhasivam | G16B 40/00 |
| 10,881,399 B2* | 1/2021 | Shelton, IV | A61B 17/1114 |
| 10,885,170 B1* | 1/2021 | Maliani | H04L 9/0643 |
| 10,966,791 B2* | 4/2021 | Harris | G16H 50/70 |
| 10,978,192 B2* | 4/2021 | Casella dos Santos | G16H 10/60 |
| 10,984,894 B2* | 4/2021 | Foley | G06T 7/0014 |
| 10,992,458 B2* | 4/2021 | Natanzon | G06F 11/1458 |
| 10,992,676 B2* | 4/2021 | Zlotnick | G06F 21/64 |
| 11,003,883 B2* | 5/2021 | Aronoff-Spencer | G16H 10/60 |
| 11,055,384 B1* | 7/2021 | Crawforth | H04L 9/3297 |
| 11,055,419 B2* | 7/2021 | Williams | H04L 9/3242 |
| 11,057,192 B2* | 7/2021 | Zheng | G06T 1/0028 |
| 11,100,533 B1* | 8/2021 | Taubeneck | H04L 9/0866 |
| 11,144,660 B2* | 10/2021 | Latka | H04L 9/3239 |
| 11,144,674 B2* | 10/2021 | Yang | G06F 21/64 |
| 11,146,403 B2* | 10/2021 | Ponnuru | H04L 9/3239 |
| 11,159,376 B2* | 10/2021 | Liebinger Portela | H04L 41/12 |
| 11,163,855 B1* | 11/2021 | Crawforth | H04L 9/3247 |
| 11,170,376 B2* | 11/2021 | Kavali | G06Q 20/02 |
| 11,194,919 B2* | 12/2021 | Karia | G06Q 20/4014 |
| 11,214,839 B2* | 1/2022 | Chowdhury | G16B 30/00 |
| 11,240,003 B2* | 2/2022 | Cao | G06F 21/645 |
| 11,244,059 B2* | 2/2022 | Yoon | G06F 21/602 |
| 11,256,712 B2* | 2/2022 | Duraisamy Soundrapandian | G06F 8/30 |
| 11,269,859 B1* | 3/2022 | Luedtke | G06F 16/245 |
| 11,270,263 B2* | 3/2022 | Shah | G06Q 10/063 |
| 11,294,999 B2* | 4/2022 | Dubeau | H04L 63/306 |
| 11,304,699 B2* | 4/2022 | Shelton, IV | A61B 34/20 |
| 11,314,891 B2* | 4/2022 | Hennebert | G06F 21/6245 |
| 11,327,950 B2* | 5/2022 | Thapar | G06Q 30/018 |
| 11,341,493 B2* | 5/2022 | Cheng | G06Q 20/389 |
| 11,362,914 B2* | 6/2022 | Jetzfellner | H04L 9/3236 |
| 11,374,738 B2* | 6/2022 | Cran | H04L 9/3239 |
| 11,386,405 B2* | 7/2022 | Pandit | G06Q 20/065 |
| 11,423,052 B2* | 8/2022 | Pandit | G06N 5/022 |
| 11,436,368 B2* | 9/2022 | Beno | G06F 21/6245 |
| 11,478,124 B2* | 10/2022 | Ninh | G16H 15/00 |
| 11,501,007 B2* | 11/2022 | Beno | G06Q 20/363 |
| 11,532,395 B2* | 12/2022 | Sharma | G06N 5/04 |
| 11,559,308 B2* | 1/2023 | Yates | A61B 17/320092 |
| 11,576,677 B2* | 2/2023 | Shelton, IV | A61M 1/73 |
| 11,618,924 B2* | 4/2023 | Chidambaran | C12Q 1/6883 514/49 |
| 11,651,096 B2* | 5/2023 | Ricotta, Jr. | H04L 9/0656 726/1 |
| 11,723,642 B2* | 8/2023 | Shelton, IV | A61B 1/000095 600/204 |
| 11,870,920 B2* | 1/2024 | Ricotta | G06F 16/9024 |
| 11,871,901 B2* | 1/2024 | Shelton, IV | G16H 40/67 |
| 11,886,421 B2* | 1/2024 | Padmanabhan | G06F 8/61 |
| 11,899,817 B2* | 2/2024 | Padmanabhan | G06F 21/64 |
| 12,002,554 B2* | 6/2024 | Hassett | G06F 40/174 |
| 12,008,232 B2* | 6/2024 | Park | H04N 21/47202 |
| 2009/0240681 A1 | 9/2009 | Saddiqi et al. | |
| 2012/0310670 A1* | 12/2012 | Pruitt | G06Q 10/10 705/2 |
| 2013/0194092 A1 | 8/2013 | Moriarty et al. | |
| 2014/0200919 A1 | 7/2014 | Malec | |
| 2017/0202605 A1 | 7/2017 | Shelton, IV et al. | |
| 2017/0372096 A1 | 12/2017 | Yousfi et al. | |
| 2018/0007320 A1* | 1/2018 | Greco | G16H 30/20 |
| 2018/0049822 A1 | 2/2018 | Henderson et al. | |
| 2018/0211010 A1 | 7/2018 | Malhotra et al. | |
| 2019/0059929 A1 | 2/2019 | Shelton, IV et al. | |
| 2019/0087542 A1 | 3/2019 | Ingraham | |
| 2019/0104919 A1 | 4/2019 | Shelton, IV et al. | |
| 2019/0200844 A1 | 7/2019 | Shelton, IV et al. | |
| 2019/0200981 A1 | 7/2019 | Harris et al. | |
| 2019/0200988 A1 | 7/2019 | Shelton, IV | |
| 2019/0201033 A1 | 7/2019 | Yates et al. | |
| 2019/0201115 A1 | 7/2019 | Shelton, IV et al. | |
| 2019/0201137 A1 | 7/2019 | Shelton, IV et al. | |
| 2019/0205441 A1 | 7/2019 | Shelton, IV et al. | |
| 2019/0205567 A1 | 7/2019 | Shelton, IV et al. | |
| 2019/0206216 A1 | 7/2019 | Shelton, IV et al. | |
| 2019/0206551 A1 | 7/2019 | Yates et al. | |
| 2019/0206562 A1 | 7/2019 | Shelton, IV et al. | |
| 2019/0206564 A1 | 7/2019 | Shelton, IV et al. | |
| 2019/0206569 A1 | 7/2019 | Shelton, IV et al. | |
| 2019/0207773 A1 | 7/2019 | Shelton, IV et al. | |
| 2019/0207911 A1 | 7/2019 | Wiener et al. | |
| 2019/0348158 A1 | 11/2019 | Livesay et al. | |
| 2020/0015907 A1 | 1/2020 | Scheib | |
| 2020/0394334 A1 | 12/2020 | Bulut et al. | |
| 2020/0405296 A1 | 12/2020 | Shelton, IV et al. | |
| 2021/0118547 A1* | 4/2021 | Morris | G16H 50/70 |
| 2021/0174415 A1* | 6/2021 | Narasimhan | G06Q 30/0248 |
| 2021/0182932 A1 | 6/2021 | Bello, Jr. | |
| 2021/0397735 A1 | 12/2021 | Samatov et al. | |
| 2022/0233102 A1 | 7/2022 | Shelton, IV et al. | |
| 2022/0233119 A1 | 7/2022 | Shelton, IV et al. | |
| 2022/0238216 A1 | 7/2022 | Shelton, IV et al. | |
| 2022/0331019 A1* | 10/2022 | Gough | A61B 90/50 |
| 2023/0026634 A1 | 1/2023 | Shelton, IV et al. | |
| 2023/0027210 A1 | 1/2023 | Shelton, IV et al. | |
| 2023/0095002 A1 | 3/2023 | Shelton, IV et al. | |
| 2023/0097906 A1 | 3/2023 | Shelton, IV et al. | |
| 2024/0013895 A1 | 1/2024 | Jin et al. | |
| 2024/0112768 A1 | 4/2024 | Shelton, IV et al. | |
| 2024/0112769 A1 | 4/2024 | Shelton, IV et al. | |
| 2024/0120041 A1 | 4/2024 | Shelton, IV et al. | |

\* cited by examiner

CAPACITY TO ADJUST PATIENT CONSENT

CROSS-REFERENCE TO RELATED APPLICATIONS

This application is related to the following, filed contemporaneously, the contents of each of which are incorporated by reference herein:
U.S. patent application Ser. No. 17/958,230, filed Sep. 30, 2022, entitled METHOD FOR HEALTH DATA AND CONSENT MANAGEMENT;
U.S. patent application Ser. No. 17/958,231, filed Sep. 30, 2022, entitled CONDITIONAL PATIENT CONSENT; and
U.S. patent application Ser. No. 17/958,235, filed Sep. 30, 2022, entitled REGION-BASED PATIENT CONSENT MANAGEMENT.

BACKGROUND

Surgical procedures are typically performed in surgical operating theaters or rooms in a healthcare facility such as, for example, a hospital. Various surgical devices and systems are utilized in performance of a surgical procedure. In the digital and information age, medical systems and facilities are often slower to implement systems or procedures utilizing newer and improved technologies due to patient safety and a general desire for maintaining traditional practices.

SUMMARY

A surgical data management system may enable a patient to provide conditional consent(s). Conditional consent by a patient may be provided for utilizing their private health data in one or more of the following: the adaptation of procedures, instrument operation, system configuration, display of results and/or plans for device usage. The patient granted consent may be associated with one or more condition(s), stipulation(s), and/or limitations of the scope, duration, and/or usage of their health data. The surgical data management system may be configured to check that patient data is only being used in accordance with the consent data (e.g., for the agreed upon purpose(s) and for the agreed upon time). In response to a data request for health data associated with a patient, the system may obtain a conditional consent associated with the patient. The system may determine whether to block access to at least a portion of the health data associated with the patient based on the data request and whether the condition(s) associated with the conditional consent have been met.

Examples of the condition associated with consent may include using the health data associated with the patient for diagnosis and/or treatment of the patient, using the health data for enhancing a surgical control program (e.g., a program configured to control a surgical instrument, a surgery planning program, a program configured to control a surgical computing system), using the health data within a privacy protection boundary, using sharable health data (e.g., a subset of health data associated with the patient), using non-patient identifying data, and/or a threshold number of datasets similar to the requested health data associated with the patient having been accumulated, using the heath data based on the occurrence of certain circumstance(s), for example, a certain clinical situation and/or a certain combination of devices, using health data within a specified time period, etc.

For example, the condition associated with conditional consent may include using the health data associated with the patient for diagnosis and/or treatment of the patient, using the health data for enhancing a surgical control program (e.g., a program configured to control a surgical instrument, a surgery planning program, a program configured to control a surgical computing system), using the health data within a privacy protection boundary, using sharable health data (e.g., a subset of health data associated with the patient), using non-patient identifying data, and/or a threshold number of datasets similar to the requested health data associated with the patient having been accumulated. For example, the system may verify that the health data is being accessed during an agreed upon time frame, and/or verify that the health data is being accessed for one or more agreed upon purposes before granting access. Based on a determination that the health data is being accessed outside of the agreed upon time frame or for a purpose other than the one or more agreed upon purposes, the processor is configured to block access to the health data. Patient identifying data may be removed from the health data associated with the patient prior to being included in the response to the data request.

A patient data system may adjust patient data access and display capabilities based on the location, the data origin, and/or the patient geographic characteristics associated with a patient data display interface. The patient data display interface may be located within or outside of the privacy protection boundary. The system may identify a region of the patient or a controlling jurisdiction of the patient's data usage. The system may determine a region-based consent requirement associated with the dataset based on the relevant controlling region and may determine whether to display the dataset via the patient data display interface based on the determined region-based consent requirement and patient consent data. The system may generate the patient data display interface based on the determining. The system may determine a regional law's bearing on patient consent and may adapt consent management accordingly.

The system may determine the geographic location of a patient data display system where the patient data display interface is to be displayed, and whether to display the dataset via the patient data display interface may be determined based on the consent requirement associated with the location of the patient data display system and patient consent data. The system may determine the data origin location of the dataset, and whether to display the dataset via the patient data display interface may be determined based on the consent requirement associated with the data origin location and patient consent data. The system may determine the patient location, and whether to display the dataset via the patient data display interface may be determined based on the consent requirement associated with the patient location and patient consent data. In some examples, the consent requirement associated with multiple regions may be used to determine whether to display the dataset.

For example, based on a determination to not display the dataset, the patient data display interface may be generated to exclude the dataset from the patient data display interface, redact the dataset on the patient data display interface and/or disable a feature associated the dataset in the patient data display interface.

A consent management system may receive a request to modify consent data associated with a patient. The consent management system may obtain patient capacity information associated with the patient and may determine whether to allow the patient to modify the consent data based on the obtained patient capacity information. The patient capacity information may indicate patient cognitive capacity, patient emotional capacity and/or the like. A response to the request to modify the consent data may be generated based on the determining. For example, based on a determination that the obtained patient capacity information indicates that patient lacks the capacity to modify the consent data, the response may indicate a rejection of the request (e.g., may indicate that the consent data may not be modified). Based on a determination that the obtained patient capacity information indicates that patient possesses the capacity to modify the consent data, the response may indicate an approval of the request (e.g., may indicate that the consent data may be modified).

For example, the consent management system may compare the patient capacity information associated with the patient to a capacity threshold. Whether to allow the patient to modify the consent data may be determined based on the comparison. In some examples, the capacity threshold may be associated with the consent modification type associated with the request. The consent data associated with the patient may include one or more consent rules (e.g., may be associated with consent conditions). The consent modification type may include at least one of granting consent, revoking consent, adding a consent rule, removing a consent rule, or modifying a consent rule. For example, the consent modification type associated with the request may be identified, and a capacity threshold used for comparison with the patient capacity information may be determined based on the consent modification type.

The consent management system may obtain surgical context information associated with the patient and may determine whether a health care provider review is required before generating the response. The determination may be based on the surgical context information and the consent modification request. The consent management system may generate a health care provider review request. Generating the request may be based on a determination that the health care provider review is required.

BRIEF DESCRIPTION OF THE DRAWINGS

Examples described herein may include a Brief Description of the Drawings

DETAILED DESCRIPTION

Figure 1:
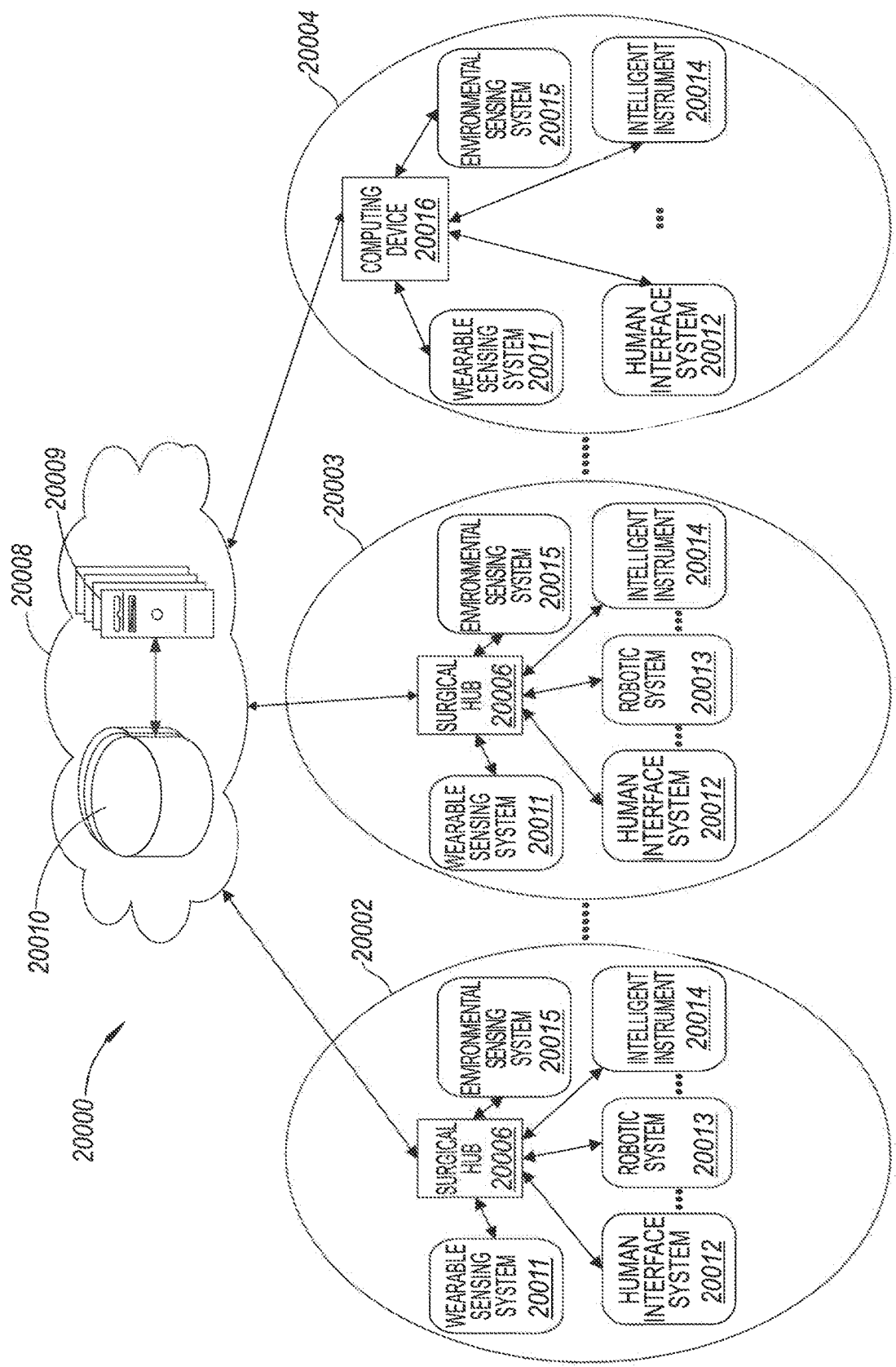
FIG. 1 is a block diagram of a computer-implemented surgical system.

FIG. 1 is a block diagram of a computer-implemented surgical system 20000. An example surgical system such as the surgical system 20000 may include one or more surgical systems (e.g., surgical sub-systems) 20002, 20003 and 20004. For example, surgical system 20002 may include a computer-implemented interactive surgical system. For example, surgical system 20002 may include a surgical hub 20006 and/or a computing device 20016 in communication with a cloud computing system 20008, for example, as described in FIG. 2. The cloud computing system 20008 may include at least one remote cloud server 20009 and at least one remote cloud storage unit 20010. Example surgical systems 20002, 20003, or 20004 may include a wearable sensing system 20011, an environmental sensing system 20015, a robotic system 20013, one or more intelligent instruments 20014, human interface system 20012, etc. The human interface system is also referred herein as the human interface device. The wearable sensing system 20011 may include one or more health care professional (HCP) sensing systems, and/or one or more patient sensing systems. The environmental sensing system 20015 may include one or more devices, for example, used for measuring one or more environmental attributes, for example, as further described in FIG. 2. The robotic system 20013 may include a plurality of devices used for performing a surgical procedure, for example, as further described in FIG. 2.

The surgical system 20002 may be in communication with a remote server 20009 that may be part of a cloud computing system 20008. In an example, the surgical system 20002 may be in communication with a remote server 20009 via an internet service provider's cable/FIOS networking node. In an example, a patient sensing system may be in direct communication with a remote server 20009. The surgical system 20002 and/or a component therein may communicate with the remote servers 20009 via a cellular transmission/reception point (TRP) or a base station using one or more of the following cellular protocols: GSM/GPRS/EDGE (2G), UMTS/HSPA (3G), long term evolution (LTE) or 4G, LTE-Advanced (LTE-A), new radio (NR) or 5G.

A surgical hub 20006 may have cooperative interactions with one of more means of displaying the image from the laparoscopic scope and information from one or more other smart devices and one or more sensing systems 20011. The surgical hub 20006 may interact with one or more sensing systems 20011, one or more smart devices, and multiple displays. The surgical hub 20006 may be configured to gather measurement data from the one or more sensing systems 20011 and send notifications or control messages to the one or more sensing systems 20011. The surgical hub 20006 may send and/or receive information including notification information to and/or from the human interface system 20012. The human interface system 20012 may include one or more human interface devices (HIDs). The surgical hub 20006 may send and/or receive notification information or control information to audio, display and/or control information to various devices that are in communication with the surgical hub.

For example, the sensing systems 20001 may include the wearable sensing system 20011 (which may include one or more HCP sensing systems and one or more patient sensing systems) and the environmental sensing system 20015 as discussed in FIG. 1. The one or more sensing systems 20001 may measure data relating to various biomarkers. The one or more sensing systems 20001 may measure the biomarkers using one or more sensors, for example, photosensors (e.g., photodiodes, photoresistors), mechanical sensors (e.g., motion sensors), acoustic sensors, electrical sensors, electrochemical sensors, thermoelectric sensors, infrared sensors, etc. The one or more sensors may measure the biomarkers as described herein using one of more of the following sensing technologies: photoplethysmography, electrocardiography, electroencephalography, colorimetry, impedimentary, potentiometry, amperometry, etc.

The biomarkers measured by the one or more sensing systems 20001 may include, but are not limited to, sleep, core body temperature, maximal oxygen consumption, physical activity, alcohol consumption, respiration rate, oxygen saturation, blood pressure, blood sugar, heart rate variability, blood potential of hydrogen, hydration state, heart rate, skin conductance, peripheral temperature, tissue perfusion pressure, coughing and sneezing, gastrointestinal motility, gastrointestinal tract imaging, respiratory tract bacteria, edema, mental aspects, sweat, circulating tumor cells, autonomic tone, circadian rhythm, and/or menstrual cycle.

The biomarkers may relate to physiologic systems, which may include, but are not limited to, behavior and psychology, cardiovascular system, renal system, skin system, nervous system, gastrointestinal system, respiratory system, endocrine system, immune system, tumor, musculoskeletal system, and/or reproductive system. Information from the biomarkers may be determined and/or used by the computer-implemented patient and the surgical system 20000, for example. The information from the biomarkers may be determined and/or used by the computer-implemented patient and the surgical system 20000 to improve said systems and/or to improve patient outcomes, for example. The one or more sensing systems 20001, biomarkers 20005, and physiological systems are described in more detail in U.S. application Ser. No. 17/156,287, titled METHOD OF ADJUSTING A SURGICAL PARAMETER BASED ON BIOMARKER MEASUREMENTS, filed Jan. 22, 2021, the disclosure of which is herein incorporated by reference in its entirety.

Figure 2:
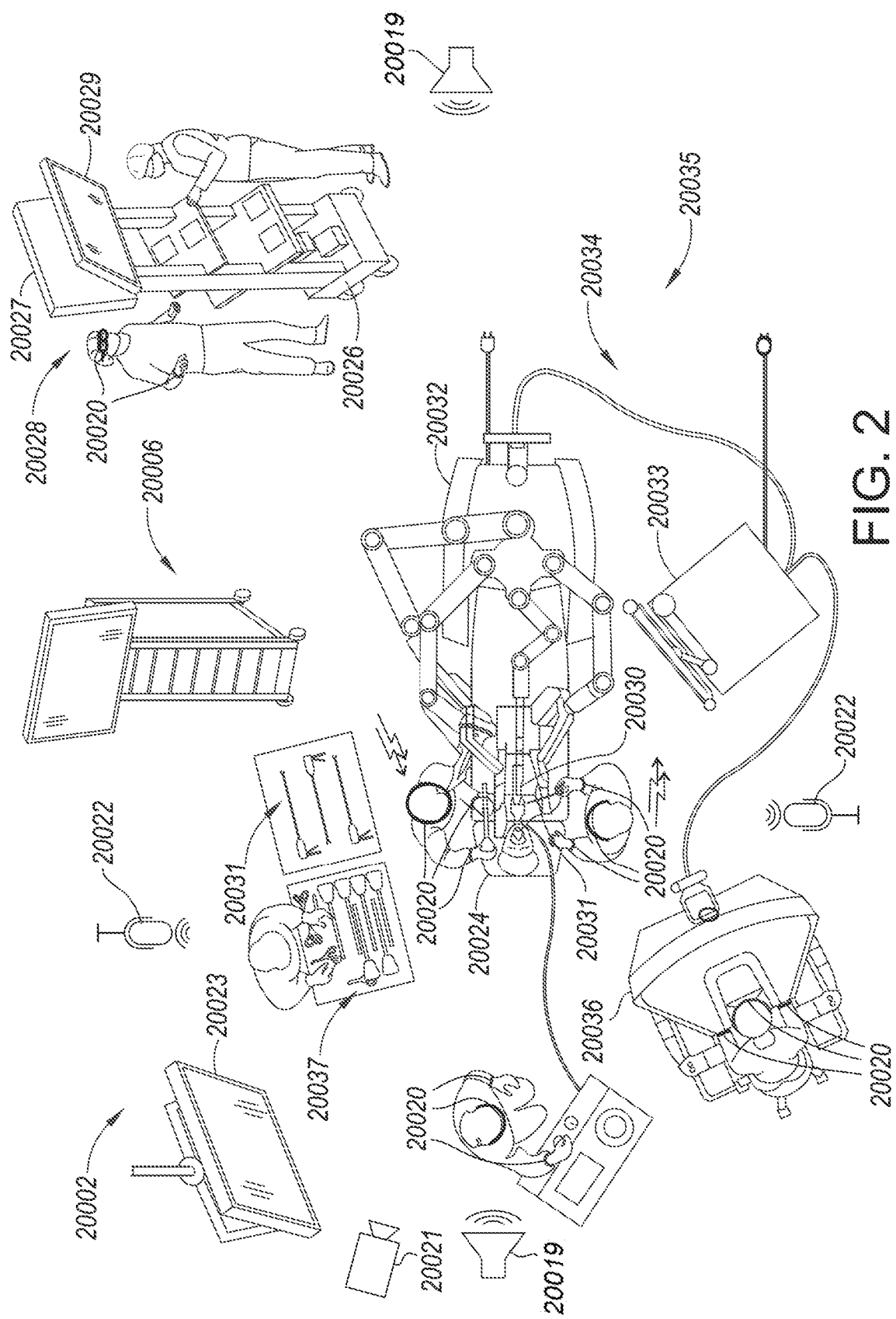
FIG. 2 shows an example surgical system in a surgical operating room.

FIG. 2 shows an example of a surgical system 20002 in a surgical operating room. As illustrated in FIG. 2, a patient is being operated on by one or more health care professionals (HCPs). The HCPs are being monitored by one or more HCP sensing systems 20020 worn by the HCPs. The HCPs and the environment surrounding the HCPs may also be monitored by one or more environmental sensing systems including, for example, a set of cameras 20021, a set of microphones 20022, and other sensors that may be deployed in the operating room. The HCP sensing systems 20020 and the environmental sensing systems may be in communication with a surgical hub 20006, which in turn may be in communication with one or more cloud servers 20009 of the cloud computing system 20008, as shown in FIG. 1. The environmental sensing systems may be used for measuring one or more environmental attributes, for example, HCP position in the surgical theater, HCP movements, ambient noise in the surgical theater, temperature/humidity in the surgical theater, etc.

As illustrated in FIG. 2, a primary display 20023 and one or more audio output devices (e.g., speakers 20019) are positioned in the sterile field to be visible to an operator at the operating table 20024. In addition, a visualization/notification tower 20026 is positioned outside the sterile field. The visualization/notification tower 20026 may include a first non-sterile human interactive device (HID) 20027 and a second non-sterile HID 20029, which may face away from each other. The HID may be a display or a display with a touchscreen allowing a human to interface directly with the HID. A human interface system, guided by the surgical hub 20006, may be configured to utilize the HIDs 20027, 20029, and 20023 to coordinate information flow to operators inside and outside the sterile field. In an example, the surgical hub 20006 may cause an HID (e.g., the primary HID 20023) to display a notification and/or information about the patient and/or a surgical procedure step. In an example, the surgical hub 20006 may prompt for and/or receive input from personnel in the sterile field or in the non-sterile area. In an example, the surgical hub 20006 may cause an HID to display a snapshot of a surgical site, as recorded by an imaging device 20030, on a non-sterile HID 20027 or 20029, while maintaining a live feed of the surgical site on the primary HID 20023. The snapshot on the non-sterile display 20027 or 20029 can permit a non-sterile operator to perform a diagnostic step relevant to the surgical procedure, for example.

In one aspect, the surgical hub 20006 may be configured to route a diagnostic input or feedback entered by a non-sterile operator at the visualization tower 20026 to the primary display 20023 within the sterile field, where it can be viewed by a sterile operator at the operating table. In one example, the input can be in the form of a modification to the snapshot displayed on the non-sterile display 20027 or 20029, which can be routed to the primary display 20023 by the surgical hub 20006.

Referring to FIG. 2, a surgical instrument 20031 is being used in the surgical procedure as part of the surgical system 20002. The hub 20006 may be configured to coordinate information flow to a display of the surgical instrument 20031. For example, in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. A diagnostic input or feedback entered by a non-sterile operator at the visualization tower 20026 can be routed by the hub 20006 to the surgical instrument display within the sterile field, where it can be viewed by the operator of the surgical instrument 20031. Example surgical instruments that are suitable for use with the surgical system 20002 are described under the heading "Surgical Instrument Hardware" and in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety, for example.

FIG. 2 illustrates an example of a surgical system 20002 being used to perform a surgical procedure on a patient who is lying down on an operating table 20024 in a surgical operating room 20035. A robotic system 20034 may be used in the surgical procedure as a part of the surgical system 20002. The robotic system 20034 may include a surgeon's console 20036, a patient side cart 20032 (surgical robot), and a surgical robotic hub 20033. The patient side cart 20032 can manipulate at least one removably coupled surgical tool 20037 through a minimally invasive incision in the body of the patient while the surgeon views the surgical site through the surgeon's console 20036. An image of the surgical site can be obtained by a medical imaging device 20030, which can be manipulated by the patient side cart 20032 to orient the imaging device 20030. The robotic hub 20033 can be used to process the images of the surgical site for subsequent display to the surgeon through the surgeon's console 20036.

Other types of robotic systems can be readily adapted for use with the surgical system 20002. Various examples of robotic systems and surgical tools that are suitable for use with the present disclosure are described in U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018, the disclosure of which is herein incorporated by reference in its entirety.

Various examples of cloud-based analytics that are performed by the cloud computing system 20008, and are suitable for use with the present disclosure, are described in U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018, the disclosure of which is herein incorporated by reference in its entirety.

In various aspects, the imaging device 20030 may include at least one image sensor and one or more optical components. Suitable image sensors may include, but are not limited to, Charge-Coupled Device (CCD) sensors and Complementary Metal-Oxide Semiconductor (CMOS) sensors.

The optical components of the imaging device 20030 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is the portion of the electromagnetic spectrum that is visible to (i.e., can be detected by) the human eye and may be referred to as visible light or simply light. A typical human eye will respond to wavelengths in air that range from about 380 nm to about 750 nm.

The invisible spectrum (e.g., the non-luminous spectrum) is the portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 20030 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

The imaging device may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information that the human eye fails to capture with its receptors for red, green, and blue. The use of multi-spectral imaging is described in greater detail under the heading "Advanced Imaging Acquisition Module" in U.S. patent application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. Multi-spectrum monitoring can be a useful tool in relocating a surgical field after a surgical task is completed to perform one or more of the previously described tests on the treated tissue. It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 20030 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Wearable sensing system 20011 illustrated in FIG. 1 may include one or more sensing systems, for example, HCP sensing systems 20020 as shown in FIG. 2. The HCP sensing systems 20020 may include sensing systems to monitor and detect a set of physical states and/or a set of physiological states of a healthcare personnel (HCP). An HCP may be a surgeon or one or more healthcare personnel assisting the surgeon or other healthcare service providers in general. In an example, a sensing system 20020 may measure a set of biomarkers to monitor the heart rate of an HCP. In an example, a sensing system 20020 worn on a surgeon's wrist (e.g., a watch or a wristband) may use an accelerometer to detect hand motion and/or shakes and determine the magnitude and frequency of tremors. The sensing system 20020 may send the measurement data associated with the set of biomarkers and the data associated with a physical state of the surgeon to the surgical hub 20006 for further processing. One or more environmental sensing devices may send environmental information to the surgical hub 20006. For example, the environmental sensing devices may include a camera 20021 for detecting hand/body position of an HCP. The environmental sensing devices may include microphones 20022 for measuring the ambient noise in the surgical theater. Other environmental sensing devices may include devices, for example, a thermometer to measure temperature and a hygrometer to measure humidity of the surroundings in the surgical theater, etc. The surgical hub 20006, alone or in communication with the cloud computing system, may use the surgeon biomarker measurement data and/or environmental sensing information to modify the control algorithms of hand-held instruments or the averaging delay of a robotic interface, for example, to minimize tremors. In an example, the HCP sensing systems 20020 may measure one or more surgeon biomarkers associated with an HCP and send the measurement data associated with the surgeon biomarkers to the surgical hub 20006. The HCP sensing systems 20020 may use one or more of the following RF protocols for communicating with the surgical hub 20006: Bluetooth, Bluetooth Low-Energy (BLE), Bluetooth Smart, Zigbee, Z-wave, IPv6 Low-power wireless Personal Area Network (6LoWPAN), Wi-Fi. The surgeon biomarkers may include one or more of the following: stress, heart rate, etc. The environmental measurements from the surgical theater may include ambient noise level associated with the surgeon or the patient, surgeon and/or staff movements, surgeon and/or staff attention level, etc.

The surgical hub 20006 may use the surgeon biomarker measurement data associated with an HCP to adaptively control one or more surgical instruments 20031. For example, the surgical hub 20006 may send a control program to a surgical instrument 20031 to control its actuators to limit or compensate for fatigue and use of fine motor skills. The surgical hub 20006 may send the control program based on situational awareness and/or the context on importance or criticality of a task. The control program may instruct the instrument to alter operation to provide more control when control is needed.

Figure 3:
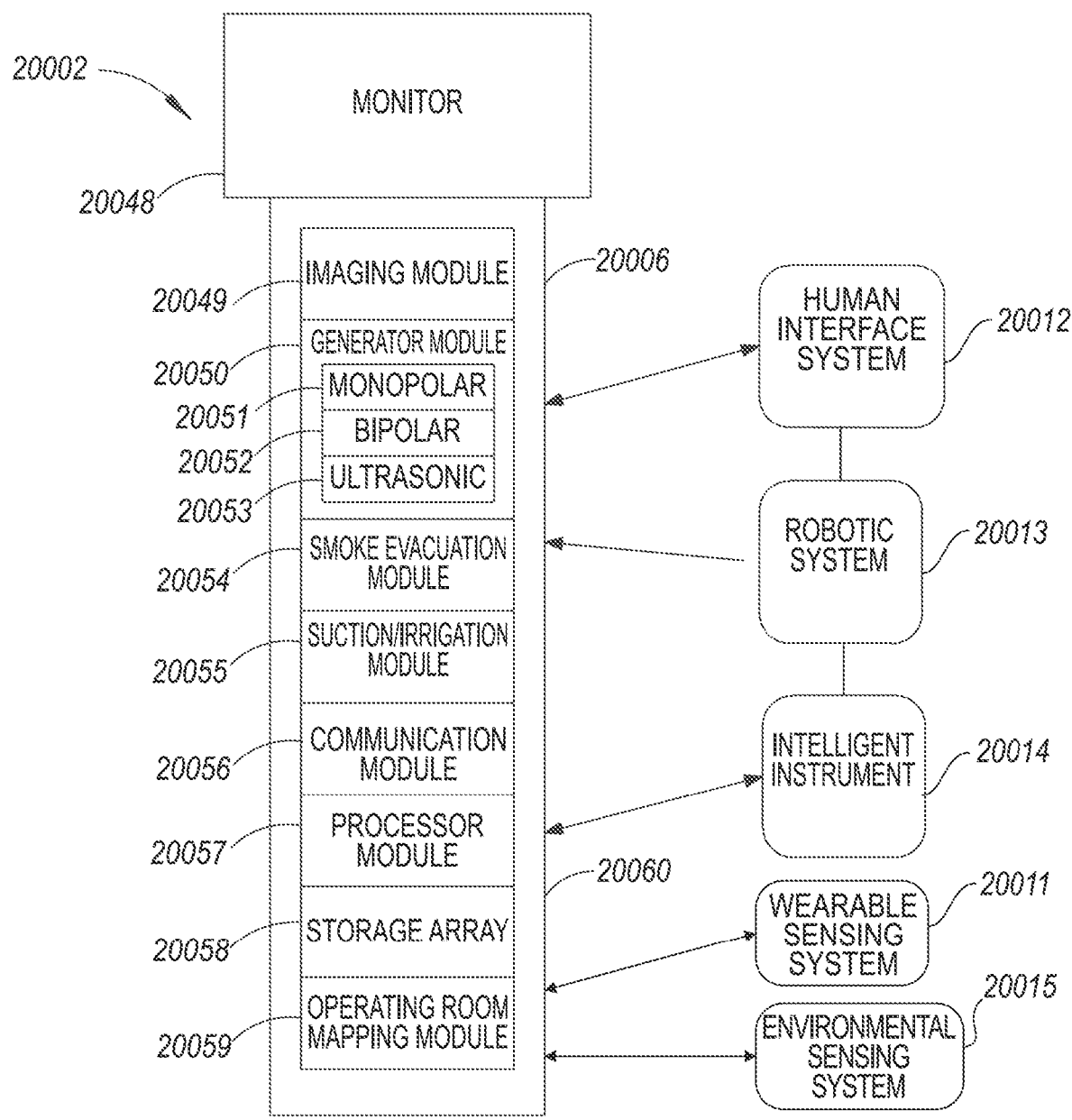
FIG. 3 illustrates an example surgical hub paired with various systems.

FIG. 3 shows an example surgical system 20002 with a surgical hub 20006. The surgical hub 20006 may be paired with, via a modular control, a wearable sensing system 20011, an environmental sensing system 20015, a human interface system 20012, a robotic system 20013, and an intelligent instrument 20014. The hub 20006 includes a display 20048, an imaging module 20049, a generator module 20050, a communication module 20056, a processor module 20057, a storage array 20058, and an operating-room mapping module 20059. In certain aspects, as illustrated in FIG. 3, the hub 20006 further includes a smoke evacuation module 20054 and/or a suction/irrigation module 20055. The various modules and systems may be connected to the modular control either directly via a router or via the communication module 20056. The operating theater devices may be coupled to cloud computing resources and data storage via the modular control. The human interface system 20012 may include a display sub-system and a notification sub-system.

The modular control may be coupled to non-contact sensor module. The non-contact sensor module may measure the dimensions of the operating theater and generate a map of the surgical theater using, ultrasonic, laser-type, and/or the like, non-contact measurement devices. Other distance sensors can be employed to determine the bounds of an operating room. An ultrasound-based non-contact sensor module may scan the operating theater by transmitting a burst of ultrasound and receiving the echo when it bounces off the perimeter walls of an operating theater as described under the heading "Surgical Hub Spatial Awareness Within an Operating Room" in U.S. Provisional patent application Ser. No. 62/611,341, titled INTERACTIVE SURGICAL PLATFORM, filed Dec. 28, 2017, which is herein incorporated by reference in its entirety. The sensor module may be configured to determine the size of the operating theater and to adjust Bluetooth-pairing distance limits. A laser-based non-contact sensor module may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 20060 offers a unified environment for managing the power, data, and fluid lines, which reduces the frequency of entanglement between such lines. Aspects of the present disclosure present a surgical hub 20006 for use in a surgical procedure that involves energy application to tissue at a surgical site. The surgical hub 20006 includes a hub enclosure 20060 and a combo generator module slidably receivable in a docking station of the hub enclosure 20060. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component. In one aspect, the fluid line may be a first fluid line, and a second fluid line may extend from the remote surgical site to a suction and irrigation module 20055 slidably received in the hub enclosure 20060. In one aspect, the hub enclosure 20060 may include a fluid interface. Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 20060 is configured to accommodate different generators and facilitate an interactive communication therebetween. One of the advantages of the hub modular enclosure 20060 is enabling the quick removal and/or replacement of various modules. Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts. Further to the above, the modular surgical enclosure also includes a second energy-generator module configured to generate a second energy, different than the first energy, for application to the tissue, and a second docking station comprising a second docking port that includes second data and power contacts, wherein the second energy generator module is slidably movable into an electrical engagement with the power and data contacts, and wherein the second energy-generator module is slidably movable out of the electrical engagement with the second power and data contacts. In addition, the modular surgical enclosure also includes a communication bus between the first docking port and the second docking port, configured to facilitate communication between the first energy-generator module and the second energy-generator module. Referring to FIG. 3, aspects of the present disclosure are presented for a hub modular enclosure 20060 that allows the modular integration of a generator module 20050, a smoke evacuation module 20054, and a suction/irrigation module 20055. The hub modular enclosure 20060 further facilitates interactive communication between the modules 20059, 20054, and 20055. The generator module 20050 can be with integrated monopolar, bipolar, and ultrasonic components supported in a single housing unit slidably insertable into the hub modular enclosure 20060. The generator module 20050 can be configured to connect to a monopolar device 20051, a bipolar device 20052, and an ultrasonic device 20053. Alternatively, the generator module 20050 may comprise a series of monopolar, bipolar, and/or ultrasonic generator modules that interact through the hub modular enclosure 20060. The hub modular enclosure 20060 can be configured to facilitate the insertion of multiple generators and interactive communication between the generators docked into the hub modular enclosure 20060 so that the generators would act as a single generator.

Figure 4:
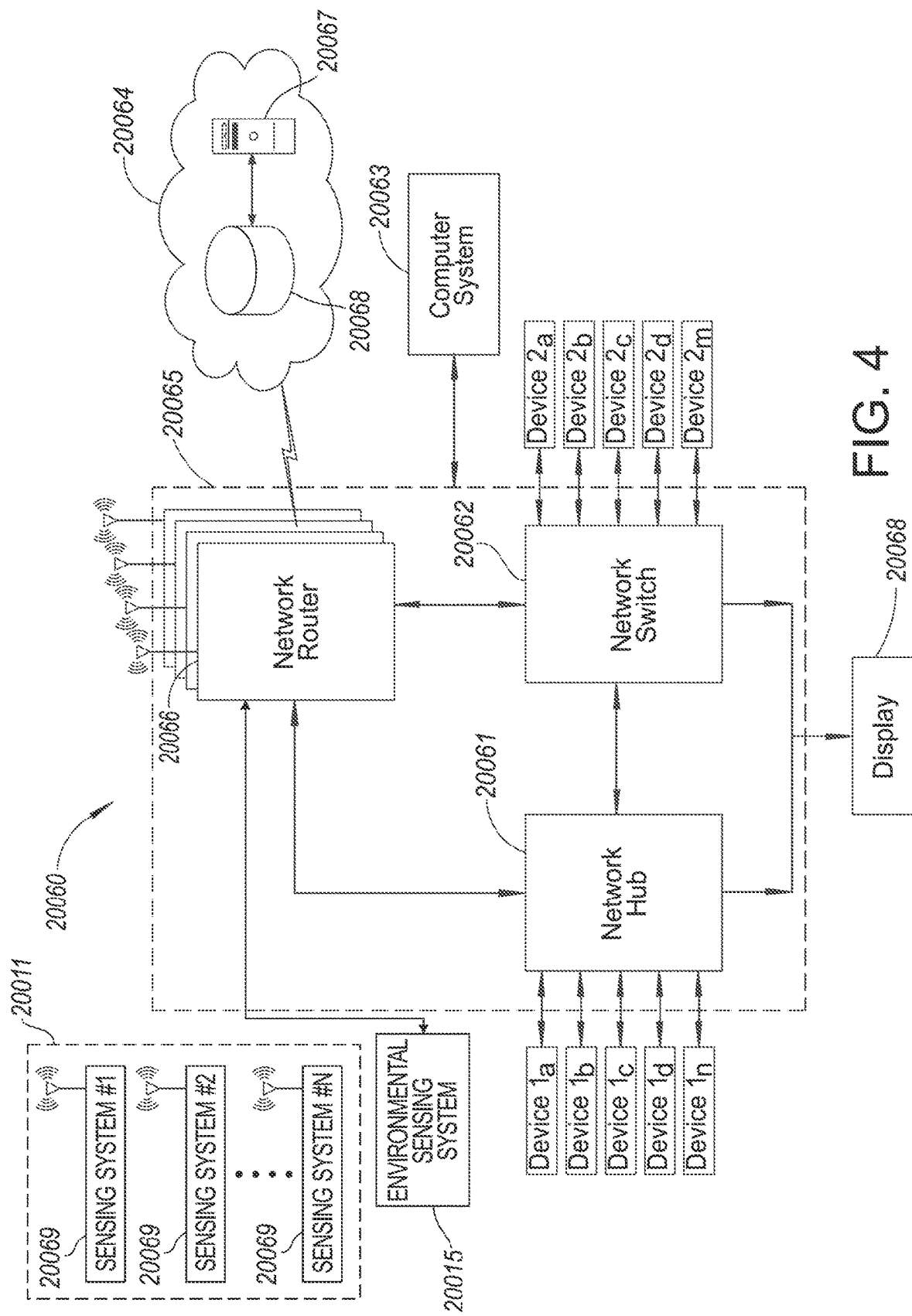
FIG. 4 illustrates a surgical data network having a set of communication surgical hubs configured to connect with a set of sensing systems, an environmental sensing system, a set of devices, etc.

FIG. 4 illustrates a surgical data network having a set of communication hubs configured to connect a set of sensing systems, environment sensing system(s), and a set of other modular devices located in one or more operating theaters of a healthcare facility, a patient recovery room, or a room in a healthcare facility specially equipped for surgical operations, to the cloud, in accordance with at least one aspect of the present disclosure.

As illustrated in FIG. 4, a surgical hub system 20060 may include a modular communication hub 20065 that is configured to connect modular devices located in a healthcare facility to a cloud-based system (e.g., a cloud computing system 20064 that may include a remote server 20067 coupled to a remote storage 20068). The modular communication hub 20065 and the devices may be connected in a room in a healthcare facility specially equipped for surgical operations. In one aspect, the modular communication hub 20065 may include a network hub 20061 and/or a network switch 20062 in communication with a network router 20066. The modular communication hub 20065 may be coupled to a local computer system 20063 to provide local computer processing and data manipulation.

The computer system 20063 may comprise a processor and a network interface 20100. The processor may be coupled to a communication module, storage, memory, non-volatile memory, and input/output (I/O) interface via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In an example, the processor may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

It is to be appreciated that the computer system 20063 may include software that acts as an intermediary between users and the basic computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

A user may enter commands or information into the computer system 20063 through input device(s) coupled to the I/O interface. The input devices may include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor 20102 through the system bus via interface port(s). The interface port(s) include, for example, a serial port, a parallel port, a game port, and a USB. The output device(s) use some of the same types of ports as input device(s). Thus, for example, a USB port may be used to provide input to the computer system 20063 and to output information from the computer system 20063 to an output device. An output adapter may be provided to illustrate that there can be some output devices like monitors, displays, speakers, and printers, among other output devices that may require special adapters. The output adapters may include, by way of illustration and not limitation, video and sound cards that provide a means of connection between the output device and the system bus. It should be noted that other devices and/or systems of devices, such as remote computer(s), may provide both input and output capabilities.

The computer system 20063 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) may be logically connected to the computer system through a network interface and then physically connected via a communication connection. The network interface may encompass communication networks such as local area networks (LANs) and wide area networks (WANs). LAN technologies may include Fiber Distributed Data Interface (FDDI), Copper Distributed Data Interface (CDDI), Ethernet/IEEE 802.3, Token Ring/IEEE 802.5, and the like. WAN technologies may include, but are not limited to, point-to-point links, circuit-switching networks like Integrated Services Digital Networks (ISDN) and variations thereon, packet-switching networks, and Digital Subscriber Lines (DSL).

In various examples, the computer system 20063 may comprise an image processor, image-processing engine, media processor, or any specialized digital signal processor (DSP) used for the processing of digital images. The image processor may employ parallel computing with single instruction, multiple data (SIMD) or multiple instruction, multiple data (MIND) technologies to increase speed and efficiency. The digital image-processing engine can perform a range of tasks. The image processor may be a system on a chip with multicore processor architecture.

The communication connection(s) may refer to the hardware/software employed to connect the network interface to the bus. While the communication connection is shown for illustrative clarity inside the computer system 20063, it can also be external to the computer system 20063. The hardware/software necessary for connection to the network interface may include, for illustrative purposes only, internal and external technologies such as modems, including regular telephone-grade modems, cable modems, optical fiber modems, and DSL modems, ISDN adapters, and Ethernet cards. In some examples, the network interface may also be provided using an RF interface.

Surgical data network associated with the surgical hub system 20060 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 20061 or network switch 20062. An intelligent surgical data network may be referred to as a manageable hub or switch. A switching hub reads the destination address of each packet and then forwards the packet to the correct port.

Modular devices 1a-1n located in the operating theater may be coupled to the modular communication hub 20065. The network hub 20061 and/or the network switch 20062 may be coupled to a network router 20066 to connect the devices 1a-1n to the cloud computing system 20064 or the local computer system 20063. Data associated with the devices 1a-1n may be transferred to cloud-based computers via the router for remote data processing and manipulation. Data associated with the devices 1a-1n may also be transferred to the local computer system 20063 for local data processing and manipulation. Modular devices 2a-2m located in the same operating theater also may be coupled to a network switch 20062. The network switch 20062 may be coupled to the network hub 20061 and/or the network router 20066 to connect the devices 2a-2m to the cloud 20064. Data associated with the devices 2a-2m may be transferred to the cloud computing system 20064 via the network router 20066 for data processing and manipulation. Data associated with the devices 2a-2m may also be transferred to the local computer system 20063 for local data processing and manipulation.

The wearable sensing system 20011 may include one or more sensing systems 20069. The sensing systems 20069 may include an HCP sensing system and/or a patient sensing system. The one or more sensing systems 20069 may be in communication with the computer system 20063 of a surgical hub system 20060 or the cloud server 20067 directly via one of the network routers 20066 or via a network hub 20061 or network switching 20062 that is in communication with the network routers 20066.

The sensing systems 20069 may be coupled to the network router 20066 to connect to the sensing systems 20069 to the local computer system 20063 and/or the cloud computing system 20064. Data associated with the sensing systems 20069 may be transferred to the cloud computing system 20064 via the network router 20066 for data processing and manipulation. Data associated with the sensing systems 20069 may also be transferred to the local computer system 20063 for local data processing and manipulation.

As illustrated in FIG. 4, the surgical hub system 20060 may be expanded by interconnecting multiple network hubs 20061 and/or multiple network switches 20062 with multiple network routers 20066. The modular communication hub 20065 may be contained in a modular control tower configured to receive multiple devices 1a-1n/2a-2m. The local computer system 20063 also may be contained in a modular control tower. The modular communication hub 20065 may be connected to a display 20068 to display images obtained by some of the devices 1a-1n/2a-2m, for example during surgical procedures. In various aspects, the devices 1a-1n/2a-2m may include, for example, various modules such as an imaging module coupled to an endoscope, a generator module coupled to an energy-based surgical device, a smoke evacuation module, a suction/irrigation module, a communication module, a processor module, a storage array, a surgical device coupled to a display, and/or a non-contact sensor module, among other modular devices that may be connected to the modular communication hub 20065 of the surgical data network.

In one aspect, the surgical hub system 20060 illustrated in FIG. 4 may comprise a combination of network hub(s), network switch(es), and network router(s) connecting the devices 1a-1n/2a-2m or the sensing systems 20069 to the cloud-base system 20064. One or more of the devices 1a-1n/2a-2m or the sensing systems 20069 coupled to the network hub 20061 or network switch 20062 may collect data in real-time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 20065 and/or computer system 20063 located in the surgical theater (e.g., a fixed, mobile, temporary, or field operating room or space) and to devices connected to the modular communication hub 20065 and/or computer system 20063 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, sensing systems, and other computerized devices located in the operating theater. The hub hardware enables multiple devices, sensing systems, and/or connections to be connected to a computer that communicates with the cloud computing resources and storage.

Applying cloud computer data processing techniques on the data collected by the devices 1a-1n/2a-2m, the surgical data network can provide improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This may include localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud computing system 20064 or the local computer system 20063 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing and using standardized approaches may provide beneficial feedback to either confirm surgical treatments and the behavior of the surgeon or suggest modifications to surgical treatments and the behavior of the surgeon.

Applying cloud computer data processing techniques on the measurement data collected by the sensing systems 20069, the surgical data network can provide improved surgical outcomes, improved recovery outcomes, reduced costs, and improved patient satisfaction. At least some of the sensing systems 20069 may be employed to assess physiological conditions of a surgeon operating on a patient or a patient being prepared for a surgical procedure or a patient recovering after a surgical procedure. The cloud-based computing system 20064 may be used to monitor biomarkers associated with a surgeon or a patient in real-time and to generate surgical plans based at least on measurement data gathered prior to a surgical procedure, provide control signals to the surgical instruments during a surgical procedure, and notify a patient of a complication during post-surgical period.

The operating theater devices 1a-1n may be connected to the modular communication hub 20065 over a wired channel or a wireless channel depending on the configuration of the devices 1a-1n to a network hub 20061. The network hub 20061 may be implemented, in one aspect, as a local network broadcast device that works on the physical layer of the Open System Interconnection (OSI) model. The network hub may provide connectivity to the devices 1a-1n located in the same operating theater network. The network hub 20061 may collect data in the form of packets and sends them to the router in half duplex mode. The network hub 20061 may not store any media access control/Internet Protocol (MAC/IP) to transfer the device data. Only one of the devices 1a-1n can send data at a time through the network hub 20061. The network hub 20061 may not have routing tables or intelligence regarding where to send information and broadcasts all network data across each connection and to a remote server 20067 of the cloud computing system 20064. The network hub 20061 can detect basic network errors such as collisions but having all information broadcast to multiple ports can be a security risk and cause bottlenecks.

The operating theater devices 2a-2m may be connected to a network switch 20062 over a wired channel or a wireless channel. The network switch 20062 works in the data link layer of the OSI model. The network switch 20062 may be a multicast device for connecting the devices 2a-2m located in the same operating theater to the network. The network switch 20062 may send data in the form of frames to the network router 20066 and may work in full duplex mode. Multiple devices 2a-2m can send data at the same time through the network switch 20062. The network switch 20062 stores and uses MAC addresses of the devices 2a-2m to transfer data.

The network hub 20061 and/or the network switch 20062 may be coupled to the network router 20066 for connection to the cloud computing system 20064. The network router 20066 works in the network layer of the OSI model. The network router 20066 creates a route for transmitting data packets received from the network hub 20061 and/or network switch 20062 to cloud-based computer resources for further processing and manipulation of the data collected by any one of or all the devices 1a-1n/2a-2m and wearable sensing system 20011. The network router 20066 may be employed to connect two or more different networks located in different locations, such as, for example, different operating theaters of the same healthcare facility or different networks located in different operating theaters of different healthcare facilities. The network router 20066 may send data in the form of packets to the cloud computing system 20064 and works in full duplex mode. Multiple devices can send data at the same time. The network router 20066 may use IP addresses to transfer data.

In an example, the network hub 20061 may be implemented as a USB hub, which allows multiple USB devices to be connected to a host computer. The USB hub may expand a single USB port into several tiers so that there are more ports available to connect devices to the host system computer. The network hub 20061 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In examples, the operating theater devices 1a-1n/2a-2m and/or the sensing systems 20069 may communicate to the modular communication hub 20065 via Bluetooth wireless technology standard for exchanging data over short distances (using short-wavelength UHF radio waves in the ISM band from 2.4 to 2.485 GHz) from fixed and mobile devices and building personal area networks (PANs). The operating theater devices 1a-1n/2a-2m and/or the sensing systems 20069 may communicate to the modular communication hub 20065 via a number of wireless or wired communication standards or protocols, including but not limited to Bluetooth, Low-Energy Bluetooth, near-field communication (NFC), Wi-Fi (IEEE 802.11 family), WiMAX (IEEE 802.16 family), IEEE 802.20, new radio (NR), long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth Low-Energy Bluetooth, Bluetooth Smart, and a second communication module may be dedicated to longer-range wireless communications such as GPS, EDGE, GPRS, CDMA, WiMAX, LTE, Ev-DO, HSPA+, HSDPA+, HSUPA+, EDGE, GSM, GPRS, CDMA, TDMA, and others.

The modular communication hub 20065 may serve as a central connection for one or more of the operating theater devices 1a-1n/2a-2m and/or the sensing systems 20069 and may handle a data type known as frames. Frames may carry the data generated by the devices 1a-1n/2a-2m and/or the sensing systems 20069. When a frame is received by the modular communication hub 20065, it may be amplified and/or sent to the network router 20066, which may transfer the data to the cloud computing system 20064 or the local computer system 20063 by using a number of wireless or wired communication standards or protocols, as described herein.

The modular communication hub 20065 can be used as a standalone device or be connected to compatible network hubs 20061 and network switches 20062 to form a larger network. The modular communication hub 20065 can be generally easy to install, configure, and maintain, making it a good option for networking the operating theater devices 1a-1n/2a-2m.

Figure 5:
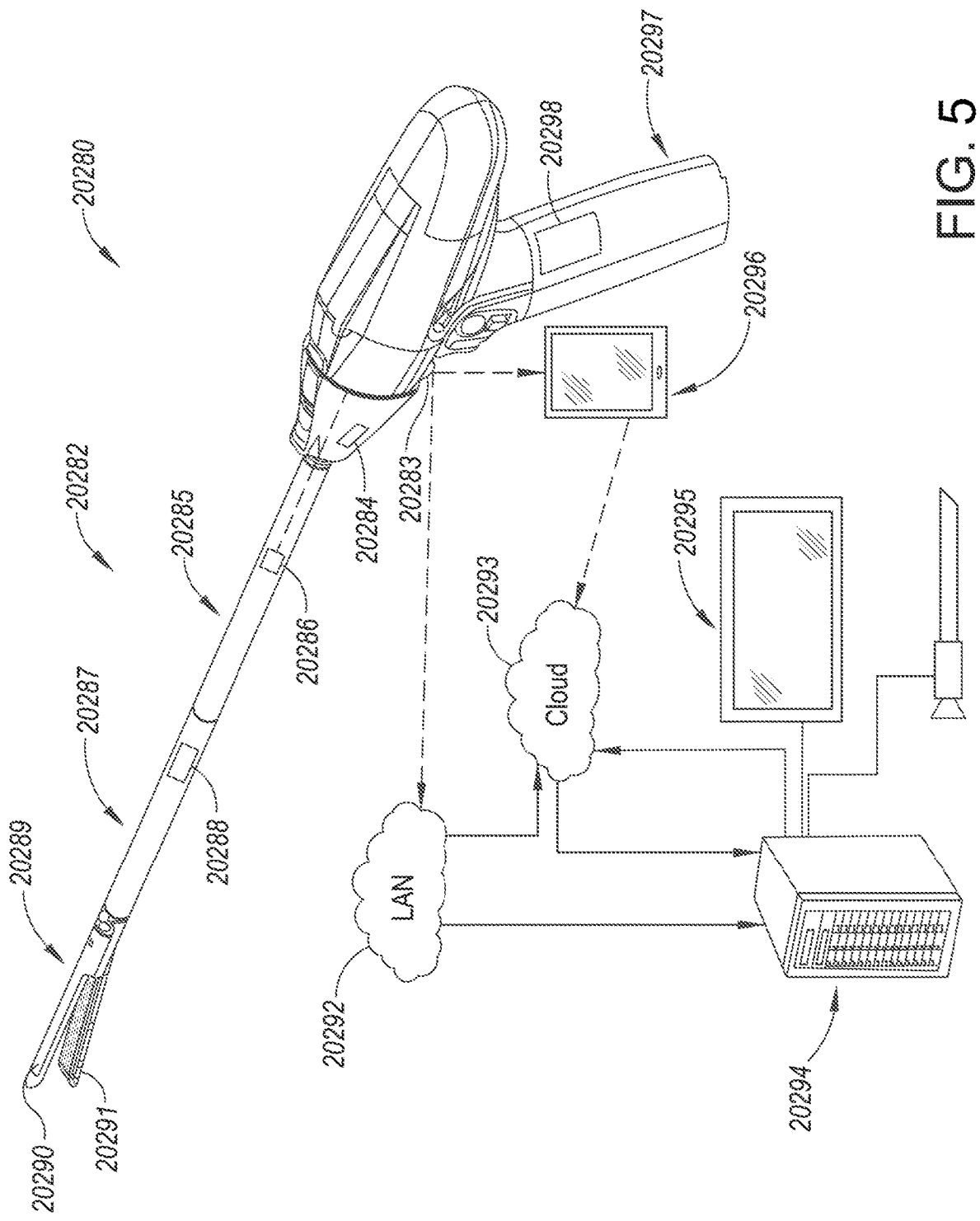
FIG. 5 shows an example surgical system that includes a handle having a controller and a motor, an adapter releasably coupled to the handle, and a loading unit releasably coupled to the adapter.

FIG. 5 illustrates an example surgical system 20280 in accordance with the present disclosure and may include a surgical instrument 20282 that can be in communication with a console 20294 or a portable device 20296 through a local area network 20292 and/or a cloud network 20293 via a wired and/or wireless connection. The console 20294 and the portable device 20296 may be any suitable computing device. The surgical instrument 20282 may include a handle 20297, an adapter 20285, and a loading unit 20287. The adapter 20285 releasably couples to the handle 20297 and the loading unit 20287 releasably couples to the adapter 20285 such that the adapter 20285 transmits a force from a drive shaft to the loading unit 20287. The adapter 20285 or the loading unit 20287 may include a force gauge (not explicitly shown) disposed therein to measure a force exerted on the loading unit 20287. The loading unit 20287 may include an end effector 20289 having a first jaw 20291 and a second jaw 20290. The loading unit 20287 may be an in-situ loaded or multi-firing loading unit (MFLU) that allows a clinician to fire a plurality of fasteners multiple times without requiring the loading unit 20287 to be removed from a surgical site to reload the loading unit 20287.

The first and second jaws 20291, 20290 may be configured to clamp tissue therebetween, fire fasteners through the clamped tissue, and sever the clamped tissue. The first jaw 20291 may be configured to fire at least one fastener a plurality of times or may be configured to include a replaceable multi-fire fastener cartridge including a plurality of fasteners (e.g., staples, clips, etc.) that may be fired more than one time prior to being replaced. The second jaw 20290 may include an anvil that deforms or otherwise secures the fasteners, as the fasteners are ejected from the multi-fire fastener cartridge.

The handle 20297 may include a motor that is coupled to the drive shaft to affect rotation of the drive shaft. The handle 20297 may include a control interface to selectively activate the motor. The control interface may include buttons, switches, levers, sliders, touchscreens, and any other suitable input mechanisms or user interfaces, which can be engaged by a clinician to activate the motor.

The control interface of the handle 20297 may be in communication with a controller 20298 of the handle 20297 to selectively activate the motor to affect rotation of the drive shafts. The controller 20298 may be disposed within the handle 20297 and may be configured to receive input from the control interface and adapter data from the adapter 20285 or loading unit data from the loading unit 20287. The controller 20298 may analyze the input from the control interface and the data received from the adapter 20285 and/or loading unit 20287 to selectively activate the motor. The handle 20297 may also include a display that is viewable by a clinician during use of the handle 20297. The display may be configured to display portions of the adapter or loading unit data before, during, or after firing of the instrument 20282.

The adapter 20285 may include an adapter identification device 20284 disposed therein and the loading unit 20287 may include a loading unit identification device 20288 disposed therein. The adapter identification device 20284 may be in communication with the controller 20298, and the loading unit identification device 20288 may be in communication with the controller 20298. It will be appreciated that the loading unit identification device 20288 may be in communication with the adapter identification device 20284, which relays or passes communication from the loading unit identification device 20288 to the controller 20298.

The adapter 20285 may also include a plurality of sensors 20286 (one shown) disposed thereabout to detect various conditions of the adapter 20285 or of the environment (e.g., if the adapter 20285 is connected to a loading unit, if the adapter 20285 is connected to a handle, if the drive shafts are rotating, the torque of the drive shafts, the strain of the drive shafts, the temperature within the adapter 20285, a number of firings of the adapter 20285, a peak force of the adapter 20285 during firing, a total amount of force applied to the adapter 20285, a peak retraction force of the adapter 20285, a number of pauses of the adapter 20285 during firing, etc.). The plurality of sensors 20286 may provide an input to the adapter identification device 20284 in the form of data signals. The data signals of the plurality of sensors 20286 may be stored within or be used to update the adapter data stored within the adapter identification device 20284. The data signals of the plurality of sensors 20286 may be analog or digital. The plurality of sensors 20286 may include a force gauge to measure a force exerted on the loading unit 20287 during firing.

The handle 20297 and the adapter 20285 can be configured to interconnect the adapter identification device 20284 and the loading unit identification device 20288 with the controller 20298 via an electrical interface. The electrical interface may be a direct electrical interface (i.e., include electrical contacts that engage one another to transmit energy and signals therebetween). Additionally, or alternatively, the electrical interface may be a non-contact electrical interface to wirelessly transmit energy and signals therebetween (e.g., inductively transfer). It is also contemplated that the adapter identification device 20284 and the controller 20298 may be in wireless communication with one another via a wireless connection separate from the electrical interface.

The handle 20297 may include a transceiver 20283 that is configured to transmit instrument data from the controller 20298 to other components of the system 20280 (e.g., the LAN 20292, the cloud 20293, the console 20294, or the portable device 20296). The controller 20298 may also transmit instrument data and/or measurement data associated with one or more sensors 20286 to a surgical hub. The transceiver 20283 may receive data (e.g., cartridge data, loading unit data, adapter data, or other notifications) from the surgical hub 20270. The transceiver 20283 may receive data (e.g., cartridge data, loading unit data, or adapter data) from the other components of the system 20280. For example, the controller 20298 may transmit instrument data including a serial number of an attached adapter (e.g., adapter 20285) attached to the handle 20297, a serial number of a loading unit (e.g., loading unit 20287) attached to the adapter 20285, and a serial number of a multi-fire fastener cartridge loaded into the loading unit to the console 20294. Thereafter, the console 20294 may transmit data (e.g., cartridge data, loading unit data, or adapter data) associated with the attached cartridge, loading unit, and adapter, respectively, back to the controller 20298. The controller 20298 can display messages on the local instrument display or transmit the message, via transceiver 20283, to the console 20294 or the portable device 20296 to display the message on the display 20295 or portable device screen, respectively.

Figure 6:
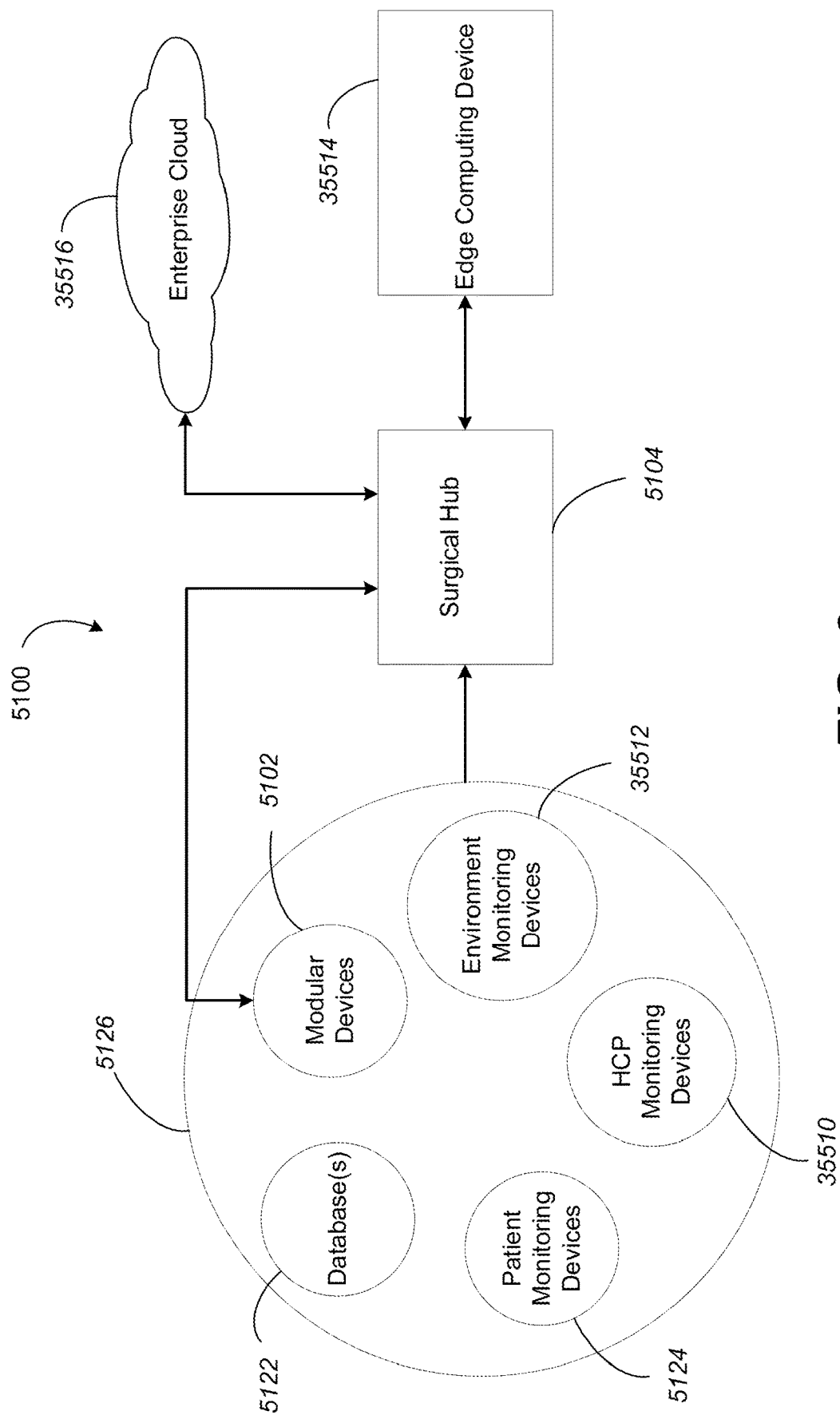
FIG. 6 shows an example situationally aware surgical system.

FIG. 6 illustrates a diagram of a situationally aware surgical system 5100, in accordance with at least one aspect of the present disclosure. The data sources 5126 may include, for example, the modular devices 5102 (which can include sensors configured to detect parameters associated with the patient, HCPs and environment and/or the modular device itself), databases 5122 (e.g., an EMR database containing patient records), patient monitoring devices 5124 (e.g., a blood pressure (BP) monitor and an electrocardiography (EKG) monitor), HCP monitoring devices 35510, and/or environment monitoring devices 35512. The surgical hub 5104 can be configured to derive the contextual information pertaining to the surgical procedure from the data based upon, for example, the particular combination(s) of received data or the particular order in which the data is received from the data sources 5126. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 5104 to derive or infer information related to the surgical procedure from received data can be referred to as "situational awareness." For example, the surgical hub 5104 can incorporate a situational awareness system, which is the hardware and/or programming associated with the surgical hub 5104 that derives contextual information pertaining to the surgical procedure from the received data and/or a surgical plan information received from the edge computing system 35514 or an enterprise cloud server 35516. Examples of different related data sources are described in U.S. patent Ser. No. 11/304,699 B2 (U.S. patent application Ser. No. 16/209,465, e.g., FIG. 35), titled METHOD FOR ADAPTIVE CONTROL SCHEMES FOR SURGICAL NETWORK CONTROL AND INTERACTION, filed Dec. 4, 2018, the disclosure of which is herein incorporated by reference in its entirety.

The situational awareness system of the surgical hub 5104 can be configured to derive the contextual information from the data received from the data sources 5126 in a variety of different ways. For example, the situational awareness system can include a pattern recognition system, or machine learning system (e.g., an artificial neural network), that has been trained on training data to correlate various inputs (e.g., data from database(s) 5122, patient monitoring devices 5124, modular devices 5102, HCP monitoring devices 35510, and/or environment monitoring devices 35512) to corresponding contextual information regarding a surgical procedure. A machine learning system can be trained to accurately derive contextual information regarding a surgical procedure from the provided inputs. In examples, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 5102. In examples, the contextual information received by the situational awareness system of the surgical hub 5104 can be associated with a particular control adjustment or set of control adjustments for one or more modular devices 5102. In examples, the situational awareness system can include a further machine learning system, lookup table, or other such system, which generates or retrieves one or more control adjustments for one or more modular devices 5102 when provided the contextual information as input.

A surgical hub 5104 incorporating a situational awareness system can provide a number of benefits for the surgical system 5100. One benefit may include improving the interpretation of sensed and collected data, which would in turn improve the processing accuracy and/or the usage of the data during the course of a surgical procedure. To return to a previous example, a situationally aware surgical hub 5104 could determine what type of tissue was being operated on; therefore, when an unexpectedly high force to close the surgical instrument's end effector is detected, the situationally aware surgical hub 5104 could correctly ramp up or ramp down the motor of the surgical instrument for the type of tissue.

The type of tissue being operated can affect the adjustments that are made to the compression rate and load thresholds of a surgical stapling and cutting instrument for a particular tissue gap measurement. A situationally aware surgical hub 5104 could infer whether a surgical procedure being performed is a thoracic or an abdominal procedure, allowing the surgical hub 5104 to determine whether the tissue clamped by an end effector of the surgical stapling and cutting instrument is lung (for a thoracic procedure) or stomach (for an abdominal procedure) tissue. The surgical hub 5104 could then adjust the compression rate and load thresholds of the surgical stapling and cutting instrument appropriately for the type of tissue.

The type of body cavity being operated in during an insufflation procedure can affect the function of a smoke evacuator. A situationally aware surgical hub 5104 could determine whether the surgical site is under pressure (by determining that the surgical procedure is utilizing insufflation) and determine the procedure type. As a procedure type can be generally performed in a specific body cavity, the surgical hub 5104 could then control the motor rate of the smoke evacuator appropriately for the body cavity being operated in. Thus, a situationally aware surgical hub 5104 could provide a consistent amount of smoke evacuation for both thoracic and abdominal procedures.

The type of procedure being performed can affect the optimal energy level for an ultrasonic surgical instrument or radio frequency (RF) electrosurgical instrument to operate at. Arthroscopic procedures, for example, may require higher energy levels because the end effector of the ultrasonic surgical instrument or RF electrosurgical instrument is immersed in fluid. A situationally aware surgical hub 5104 could determine whether the surgical procedure is an arthroscopic procedure. The surgical hub 5104 could then adjust the RF power level or the ultrasonic amplitude of the generator (e.g., "energy level") to compensate for the fluid filled environment. Relatedly, the type of tissue being operated on can affect the optimal energy level for an ultrasonic surgical instrument or RF electrosurgical instrument to operate at. A situationally aware surgical hub 5104 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 5104 can be configured to adjust the energy level for the ultrasonic surgical instrument or RF electrosurgical instrument throughout the course of a surgical procedure, rather than just on a procedure-by-procedure basis. A situationally aware surgical hub 5104 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

In examples, data can be drawn from additional data sources 5126 to improve the conclusions that the surgical hub 5104 draws from one data source 5126. A situationally aware surgical hub 5104 could augment data that it receives from the modular devices 5102 with contextual information that it has built up regarding the surgical procedure from other data sources 5126. For example, a situationally aware surgical hub 5104 can be configured to determine whether hemostasis has occurred (e.g., whether bleeding at a surgical site has stopped) according to video or image data received from a medical imaging device. The surgical hub 5104 can be further configured to compare a physiologic measurement (e.g., blood pressure sensed by a BP monitor communicably connected to the surgical hub 5104) with the visual or image data of hemostasis (e.g., from a medical imaging device communicably coupled to the surgical hub 5104) to make a determination on the integrity of the staple line or tissue weld. The situational awareness system of the surgical hub 5104 can consider the physiological measurement data to provide additional context in analyzing the visualization data. The additional context can be useful when the visualization data may be inconclusive or incomplete on its own.

For example, a situationally aware surgical hub 5104 could proactively activate the generator to which an RF electrosurgical instrument is connected if it determines that a subsequent step of the procedure requires the use of the instrument. Proactively activating the energy source can allow the instrument to be ready for use as soon as the preceding step of the procedure is completed.

The situationally aware surgical hub 5104 could determine whether the current or subsequent step of the surgical procedure requires a different view or degree of magnification on the display according to the feature(s) at the surgical site that the surgeon is expected to need to view. The surgical hub 5104 could proactively change the displayed view (supplied by, e.g., a medical imaging device for the visualization system) accordingly so that the display automatically adjusts throughout the surgical procedure.

The situationally aware surgical hub 5104 could determine which step of the surgical procedure is being performed or will subsequently be performed and whether particular data or comparisons between data will be required for that step of the surgical procedure. The surgical hub 5104 can be configured to automatically call up data screens based upon the step of the surgical procedure being performed, without waiting for the surgeon to ask for the particular information.

Errors may be checked during the setup of the surgical procedure or during the course of the surgical procedure. For example, the situationally aware surgical hub 5104 could determine whether the operating theater is setup properly or optimally for the surgical procedure to be performed. The surgical hub 5104 can be configured to determine the type of surgical procedure being performed, retrieve the corresponding checklists, product location, or setup needs (e.g., from a memory), and then compare the current operating theater layout to the standard layout for the type of surgical procedure that the surgical hub 5104 determines is being performed. In some exemplifications, the surgical hub 5104 can compare the list of items for the procedure and/or a list of devices paired with the surgical hub 5104 to a recommended or anticipated manifest of items and/or devices for the given surgical procedure. If there are any discontinuities between the lists, the surgical hub 5104 can provide an alert indicating that a particular modular device 5102, patient monitoring device 5124, HCP monitoring devices 35510, environment monitoring devices 35512, and/or other surgical item is missing. In some examples, the surgical hub 5104 can determine the relative distance or position of the modular devices 5102 and patient monitoring devices 5124 via proximity sensors, for example. The surgical hub 5104 can compare the relative positions of the devices to a recommended or anticipated layout for the particular surgical procedure. If there are any discontinuities between the layouts, the surgical hub 5104 can be configured to provide an alert indicating that the current layout for the surgical procedure deviates from the recommended layout.

The situationally aware surgical hub 5104 could determine whether the surgeon (or other HCP(s)) was making an error or otherwise deviating from the expected course of action during the course of a surgical procedure. For example, the surgical hub 5104 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 5104 determined is being performed. The surgical hub 5104 can provide an alert indicating that an unexpected action is being performed or an unexpected device is being utilized at the particular step in the surgical procedure.

The surgical instruments (and other modular devices 5102) may be adjusted for the particular context of each surgical procedure (such as adjusting to different tissue types) and validating actions during a surgical procedure. Next steps, data, and display adjustments may be provided to surgical instruments (and other modular devices 5102) in the surgical theater according to the specific context of the procedure.

Figure 7:
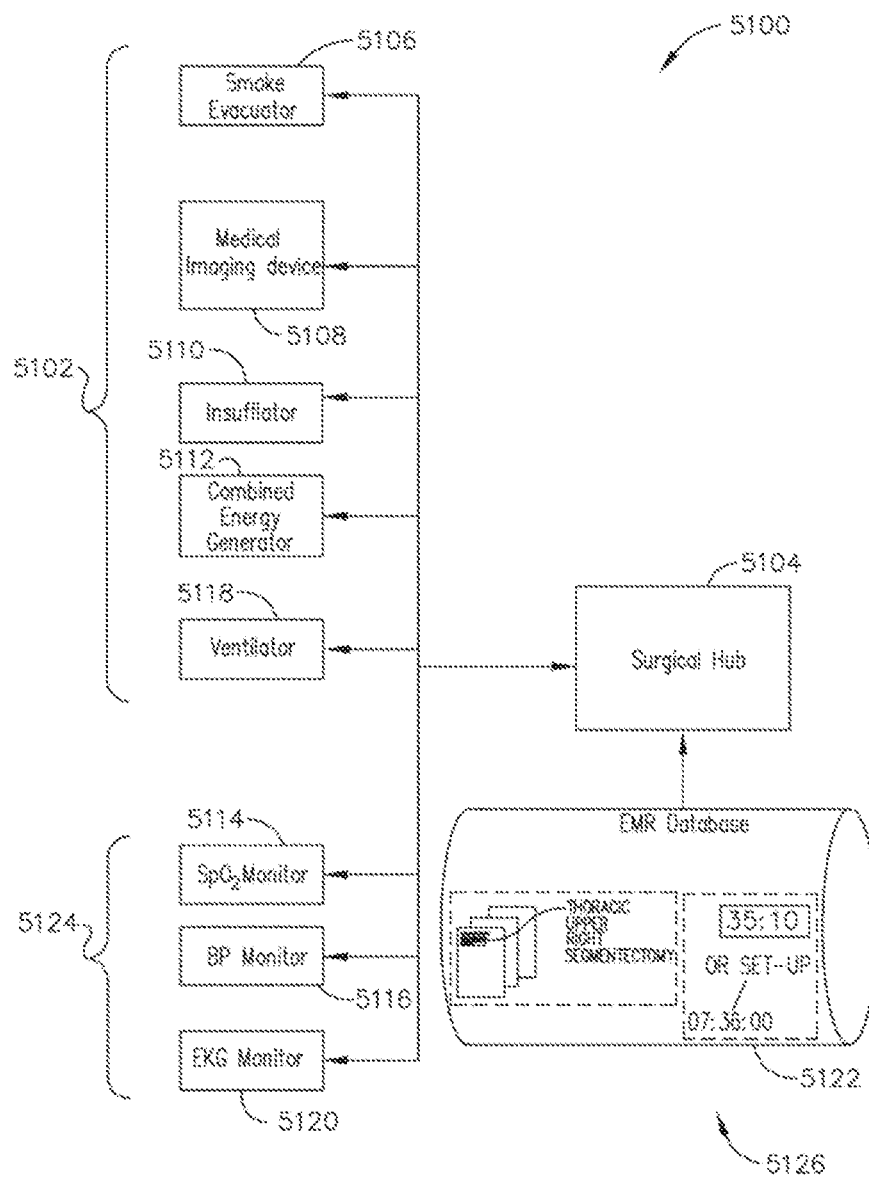
FIG. 7 illustrates a diagram of a surgical hub communicably coupled to a particular set of modular devices and an Electronic Medical Record (EMR) database.

FIG. 7 illustrates a diagram of a surgical hub communicably coupled to a particular set of modular devices and an Electronic Medical Record (EMR) database. FIG. 7 illustrates a diagram of a surgical system 5100 including a surgical hub 5104 communicably coupled to a particular set of data sources 5126. A surgical hub 5104 including a situational awareness system may utilize the data received from the data sources 5126 to derive contextual information regarding the surgical procedure that the surgical hub 5104, the modular devices 5102 paired to the surgical hub 5104, and the patient monitoring devices 5124 paired to the surgical hub 5104 are being utilized in connection with. The inferences (i.e., contextual information) that the situational awareness system may derive from the particular set of data sources 5126 are depicted in dashed boxes extending from the data source(s) 5126 from which they are derived. The contextual information derived from the data sources 5126 may include, for example, what step of the surgical procedure is being performed, whether and how a particular modular device 5102 is being used, and the patient's condition.

In the example illustrated in FIG. 7, the data sources 5126 may include a database 5122, a variety of modular devices 5102, and a variety of patient monitoring devices 5124. The surgical hub 5104 may be connected to various databases 5122 to retrieve therefrom data regarding the surgical procedure that is being performed or is to be performed. In one exemplification of the surgical system 5100, the databases 5122 may include an EMR database of a hospital. The data that may be received by the situational awareness system of the surgical hub 5104 from the databases 5122 may include, for example, start (or setup) time or operational information regarding the procedure (e.g., a segmentectomy in the upper right portion of the thoracic cavity). The surgical hub 5104 may derive contextual information regarding the surgical procedure from this data alone or from the combination of this data and data from other data sources 5126.

The surgical hub 5104 may be connected to (e.g., paired with) a variety of patient monitoring devices 5124. In an example of the surgical system 5100, the patient monitoring devices 5124 that are be paired with the surgical hub 5104 may include a pulse oximeter (SpO2 monitor) 5114, a BP monitor 5116, and an EKG monitor 5120. The perioperative data that is received by the situational awareness system of the surgical hub 5104 from the patient monitoring devices 5124 may include, for example, the patient's oxygen saturation, blood pressure, heart rate, and other physiological parameters. The contex-tual information that may be derived by the surgical hub 5104 from the perioperative data transmitted by the patient monitoring devices 5124 may include, for example, whether the patient is located in the operating theater or under anesthesia. The surgical hub 5104 may derive these inferences from data from the patient monitoring devices 5124 alone or in combination with data from other data sources 5126 (e.g., the ventilator 5118).

The surgical hub 5104 may be connected to (e.g., paired with) a variety of modular devices 5102. In one exemplification of the surgical system 5100, the modular devices 5102 that are paired with the surgical hub 5104 may include a smoke evacuator 5106, a medical imaging device 5108, an insufflator 5110, a combined energy gen-erator 5112 (for powering an ultrasonic surgical instrument and/or an RF electrosurgical instrument), and a ventilator 5118.

The medical imaging device 5108 may include an optical component and an image sensor that generates image data. The optical component may include lens or a light source, for example. The image sensor may include a charge-coupled device (CCD) or a complementary metal-oxide-semicon-ductor (CMOS), for example. In various examples, the medical imaging device 5108 may include an endoscope, a laparoscope, a thoracoscope, and other such imaging devices. Various additional components of the medical imaging device 5108 are described herein. The perioperative data that is received by the surgical hub 5104 from the medical imaging device 5108 may include, for example, whether the medical imaging device 5108 is activated and a video or image feed. The contextual information that is derived by the surgical hub 5104 from the perioperative data transmitted by the medical imaging device 5108 may include, for example, whether the procedure is a VATS procedure (based on whether the medical imaging device 5108 is activated or paired to the surgical hub 5104 at the beginning or during the course of the procedure). Furthermore, the image or video data from the medical imaging device 5108 (or the data stream representing the video for a digital medical imaging device 5108) may be processed by a pattern recognition system or a machine learning system to recognize features (e.g., organs or tissue types) in the field of view (FOY) of the medical imaging device 5108, for example. The contextual information that is derived by the surgical hub 5104 from the recognized features may include, for example, what type of surgical procedure (or step thereof) is being performed, what organ is being operated on, or what body cavity is being operated in.

Figure 8:
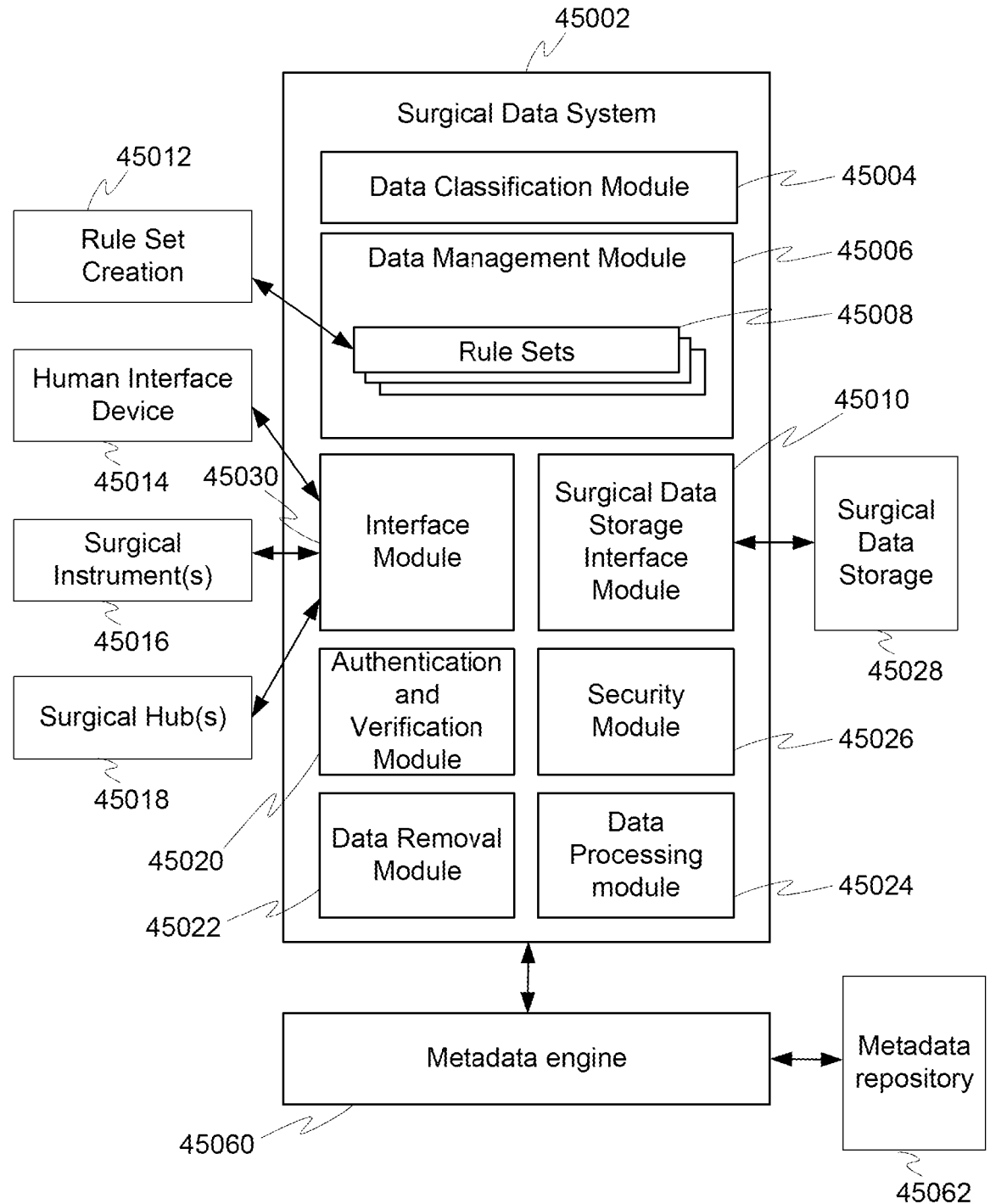
FIG. 8 shows an example surgical data system.

FIG. 8 shows an example surgical data system. The surgical data system 45002 may support functionalities of a surgical hub, for example, the surgical hub 20006 in FIG. 3. The surgical data system 45002 may support functionalities of various modules of a surgical hub, for example, the various modules in the surgical hub 20006 of FIG. 3. The surgical data system 45002 may be part of a surgical hub, for example, the surgical hub 20006 in FIG. 3. The surgical data system 45002 may be part of a processor module of a surgical hub, for example, the processor module 20057 of the surgical hub 20006. The surgical data system 45002 may be a stand-alone system.

The surgical data system 45002 may include any hardware and/or software suitable for providing functionalities of managing and processing surgical information. The surgical data system 45002 may provide functionalities to support the structure and/or functions described in connection with FIGS. 1-18 herein. For example, the surgical data system 45002 may support one or more elements of a computer-implemented interactive surgical system 20070 in FIG. 5. Examples of data processing that are suitable for use with the surgical data system 45002 are described in U.S. Patent Application Publication No. US 2019-0201033 A1 (U.S. patent application Ser. No. 15/940,663), titled SURGICAL SYSTEM DISTRIBUTED PROCESSING, filed Mar. 29, 2018, the disclosure of which is herein incorporated by reference in its entirety. In one or more of those examples, processing of data may be shared with a handheld instrument with a limited processor. The surgical data system 45002 may include a situational awareness system that is described herein. Examples that are suitable for use with the surgical data system 45002 are described in U.S. Patent Application Publication No. US 2019-0206551 A1 (U.S. patent application Ser. No. 15/940,666), titled SPATIAL AWARENESS OF SURGICAL HUBS IN OPERATING ROOMS, filed Mar. 29, 2018, the disclosure of which is herein incorporated by reference in its entirety. In one or more of those examples, a surgical hub may identify the bounds of an operating space.

The surgical data system 45002 may include one or more functional modules. Each module may include hardware, software, or a combination thereof that enable functionality of the module. One or more modules, operating in concert or otherwise, may enable authentication and verification of data, data security, database integration, data classification, data processing, data removal and big data management. The modules may include hardware elements, such as a computer processing unit, a graphics processing unit, a field-programmable gate array (FPGAs), communications hardware, memory, and the like. The modules may include software elements that when executed by a processor cause the modules to perform the functionalities of the modules.

The surgical data system 45002 may include an interface module 45030. The interface module 45030 may enable communication with one or more of a human interface device 45014, a surgical instrument 45016, or a surgical hub 45018 (e.g., surgical hub 5104). The human interface device 45014 may include a display. In some examples, the surgical hub 45018 may be the surgical hub 20006 that has a communication module 20056. The surgical data system 45002 may include, for example, one or more surgical data repositories. The surgical data system 45002 may interact with a surgical data storage 45028 through the surgical data storage interface module 45010. In an example, the surgical data storage 45028 may include the remote server 20067 of the cloud computing system 20064 in FIG. 4.

The surgical data system 45002, may obtain data, for example, from various operating room equipment and sensing devices, as shown in FIG. 2. For example, the data may include any surgical data collected from the various operating room equipment and sensing devices. For example, the surgical data system 45002 may receive data directly from any of the networked devices disclosed in FIGS. 1-8. Such data may include information about a live surgical procedure, for example. Such data may include information about a past surgical procedure. Such data may include information about future, scheduled surgical procedures. Examples of data this is suitable for use with the present disclosure are described in U.S. Patent Application Publication No. US 2019-0207773 A1 (U.S. patent application Ser. No. 15/940, 645), titled SELF DESCRIBING DATA PACKETS GENERATED AT AN ISSUING INSTRUMENT, filed Mar. 29, 2018, the disclosure of which is herein incorporated by reference in its entirety. In one or more of those examples, self-describing data may allow a processor to interpret data without having been told in advance of its receipt.

Information about surgical procedures (e.g., surgical information) may include information about the patient, the staff, the procedure as planned, the procedure as experienced, and post-operative activity including patient outcomes. For example, the information received and used by the surgical data system 45002 may include patient records, patient imaging, models of patient anatomy, patient lab results, patient medical history, and the like. For example, the information received and used by the surgical data system 45002 may include a staff manifest for a procedure, details about the past procedures of the specific staff members, staff metrics, experience, recent scheduling and workload, and historical surgical activity, such instrument use statistics, procedure duration, and the like. For example, the information received and used by the surgical data system 45002 may include procedure plans, equipment and inventory information, pull-lists, checklists, procedure plan analysis and recommendations. For example, the information received and used by the surgical data system 45002 may include any data collected or generated during a live procedure, such as procedure progress, milestones, patient information, vitals, operating theater setup, staff movement, imaging, instrument use, surgical technique, such as that captured by video, recorded manually, and/or inferred from smart-instrument reporting for example, duration, abnormal event reporting, and the like. Any data captured during a live procedure may also be stored and made available as a past procedure. For example, the information received and used by the surgical data system 45002 may include post-operative records, patient recovery information, and patient outcome information, post-operative diagnostic information, such as labs, imaging, etc.

The surgical data system 45002 may include authentication and verification module 45020. The authentication and verification module 45020 may authenticate and/or verify surgical data that the device receives by employing the surgical data system 45002. Examples that are suitable for use with the authentication and verification module 45020 are described in in U.S. Patent Application Publication No. US 2019-0205441 A1 (U.S. patent application Ser. No. 16/182,224), titled SURGICAL NETWORK, INSTRUMENT, AND CLOUD RESPONSES BASED ON VALIDATION OF RECEIVED DATASET AND AUTHENTICATION OF ITS SOURCE AND INTEGRITY, filed Nov. 6, 2018, the disclosure of which is herein incorporated by reference in its entirety. In one or more of those examples, hub, instrument, and cloud responses may operate based on validation of a received dataset and authentication of its source and integrity. One or more of the responses may be a choice of reactions to either the data or metadata.

The surgical data system 45002 may include security module 45026. In an example, the security module 45026 may provide security of monitoring authenticity and sterility of manual device(s) assisting in a robotic case. Examples that are suitable for use with the security module 45026 are described in in U.S. Patent Application Publication No. US 2019-0207911 A1 (U.S. patent application Ser. No. 15/940, 641), titled INTERACTIVE SURGICAL SYSTEMS WITH ENCRYPTED COMMUNICATIONS CAPABILITIES, filed Mar. 29, 2018, the disclosure of which is herein incorporated by reference in its entirety. In one or more of those examples, mantle generator data may be encrypted and communicated through the internet. Examples that are suitable for use with the security module 45026 are described in in U.S. Patent Application Publication No. US 2019-0206216 A1 (U.S. patent application Ser. No. 16/182,248), titled DETECTION AND ESCALATION OF SECURITY RESPONSES OF SURGICAL INSTRUMENTS TO INCREASING SEVERITY THREATS, filed Nov. 6, 2018, the disclosure of which is herein incorporated by reference in its entirety. In one or more of those examples, a wireless pair surgical instrument may detect and escalate security responses to numerous or increasing severity threats.

The surgical data system 45002 may include a data management module 45006. The data management module 45006 may provide management of a data stream, and/or an organization and structure of the data stream, for example, to facilitate an integration of the data stream into a database or multiple databases. The data management module 45006 may provide management of a data stream, and/or an organization and structure of the data stream, for example, by selecting one or more rule sets from rule sets 45008. The rule sets 45008 may be generated via rule set creation 45012. Examples that are suitable for use with the data management module 45006 are described in in U.S. Patent Application Publication No. 2019-0200988 A1 (U.S. patent application Ser. No. 16/024,162), titled SURGICAL SYSTEMS WITH PRIORITIZED DATA TRANSMISSION CAPABILITIES, filed Jun. 29, 2018, the disclosure of which is herein incorporated by reference in its entirety. In one or more of those examples, same data that is received from two different sources may be prioritized. Examples that are suitable for use with the security module 45026 are described in in U.S. Patent Application Publication No. US 2019-0205567 A1 (U.S. patent application Ser. No. 15/940,649), titled DATA PAIRING TO INTERCONNECT A DEVICE MEASURED PARAMETER WITH AN OUTCOME, filed Mar. 29, 2018, the disclosure of which is herein incorporated by reference in its entirety. In one or more of those examples, a data pairing method may allow a surgical hub to interconnect a device measured parameter with an outcome.

The surgical data system 45002 may communicate with a metadata engine 45060. A metadata engine may collect, store (e.g., in short-term), and/or analyze information about data and/or metadata in use within a domain. For example, the metadata engine 45060 may manage metadata harvesting, register metadata, categorize metadata, organize metadata, develop a scheme for metadata storage, and/or manage metadata tagging. Metadata may include data about data such as content data. Metadata may include digital media, catalog(s), dictionar(ies), and taxonom(ies). In examples, metadata of a dataset may include one or more of the following: a title, an indication of a datatype, the number of entries in a dataset, maximum and/or minimum value in the dataset, the number of attributes indicated by the dataset, the lineage of the dataset (e.g., who created an entry, who accessed the dataset at what time, how the dataset was changed, etc.). For example, metadata of a dataset collected from a powered stapler generator during a gastric bypass surgery may include data of tissue type. Metadata harvesting (or metadata discovery) may include discovering the semantics of a data element in a dataset using automated tool(s). For example, an output of a metadata discovery may include a set of mappings between data source elements and a centralized metadata registry. Metadata in one or more examples herein may be discovered using spatial functions and/or spatial predicates. Spatial functions may be used to modify features to create additional features (e.g., creating new features from existing ones), for example, by providing a buffer around them, intersecting features, etc. Spatial predicates may use true/false queries about spatial relationships between geometries. Metadata tagging (e.g., adding information about a dataset) may be used to indicate compilation information associated with a respective dataset, for example, when the dataset is added to a database and/or indicate result(s) based on an inclusion of the dataset in the database. Metadata in one or more examples herein may be registered in a metadata registry. Metadata definitions (e.g., all metadata definitions for an organization) may be stored in the metadata registry and/or maintained in a controlled manner. In examples, metadata registry may be placed at a central and/or secured location in an organization. Metadata in one or more examples herein may be stored in a metadata repository (e.g., a metadata repository 45062). A metadata repository is the database where metadata (e.g., all metadata for an organization) is stored. The metadata registry may indicate relationships among related metadata types, for example, related metadata types in the metadata repository. In examples, the metadata engine may communicate with the surgical data system 45002 through the interface module 45030. Examples of metadata are described in U.S. patent application Ser. No. 17/384,337), titled SURGICAL DATA SYSTEM AND CONTROL, filed Jul. 23, 2021, the disclosure of which is herein incorporated by reference in its entirety.

Conditional consent by a patient may be provided for utilizing their private health data in the adaptation of procedures, instrument operation, system configuration, display of results and/or plans for device usage. The consent of the patient could be limited. Consent may be associated with conditions, stipulations, and/or limitations of the breadth, durability or usage of the patient's private data. For example, the consent of the patient may be conditioned upon an occurrence of certain circumstance(s). For example, the consent of the patient may be conditioned upon certain clinical situation(s) and/or combination of devices. The consent may be associated with one or more limitations, which may be used to control the magnitude of the data shared and/or the extent to which the data is allowed to be shared. For example, the limitation(s) may pertain to transmission of data outside of a Health Insurance Portability and Accountability Act (HIPAA)-protected network at which the patient is being treated and/or diagnosed. For example, the limitations may pertain to the level(s) of a connected digital ecosystem that can access the specific patient data and in what state the patient data may be accessed. For example, the limitations may pertain to the state in which a connected digital ecosystem can access the patient data. For example, a patient's preferences on consent may be archived, recorded and/or cataloged for determining whether at least a portion of the patient health records may be used for sharing, combining, and/or using within a larger database of surgical jobs, outcomes, constraints. The patient's preferences on consent may be archived, recorded and/or cataloged for identifying which portion(s) of the patient health records may be used for sharing, combining, and/or using within a larger database of surgical jobs, outcomes, constraints. For example, patient consent may be used to control the access and/or use of the patient's health record with other patient health records to determine patterns, improvements, and/or techniques that may be used to affect the operation of surgical tools for future use.

Figure 9:
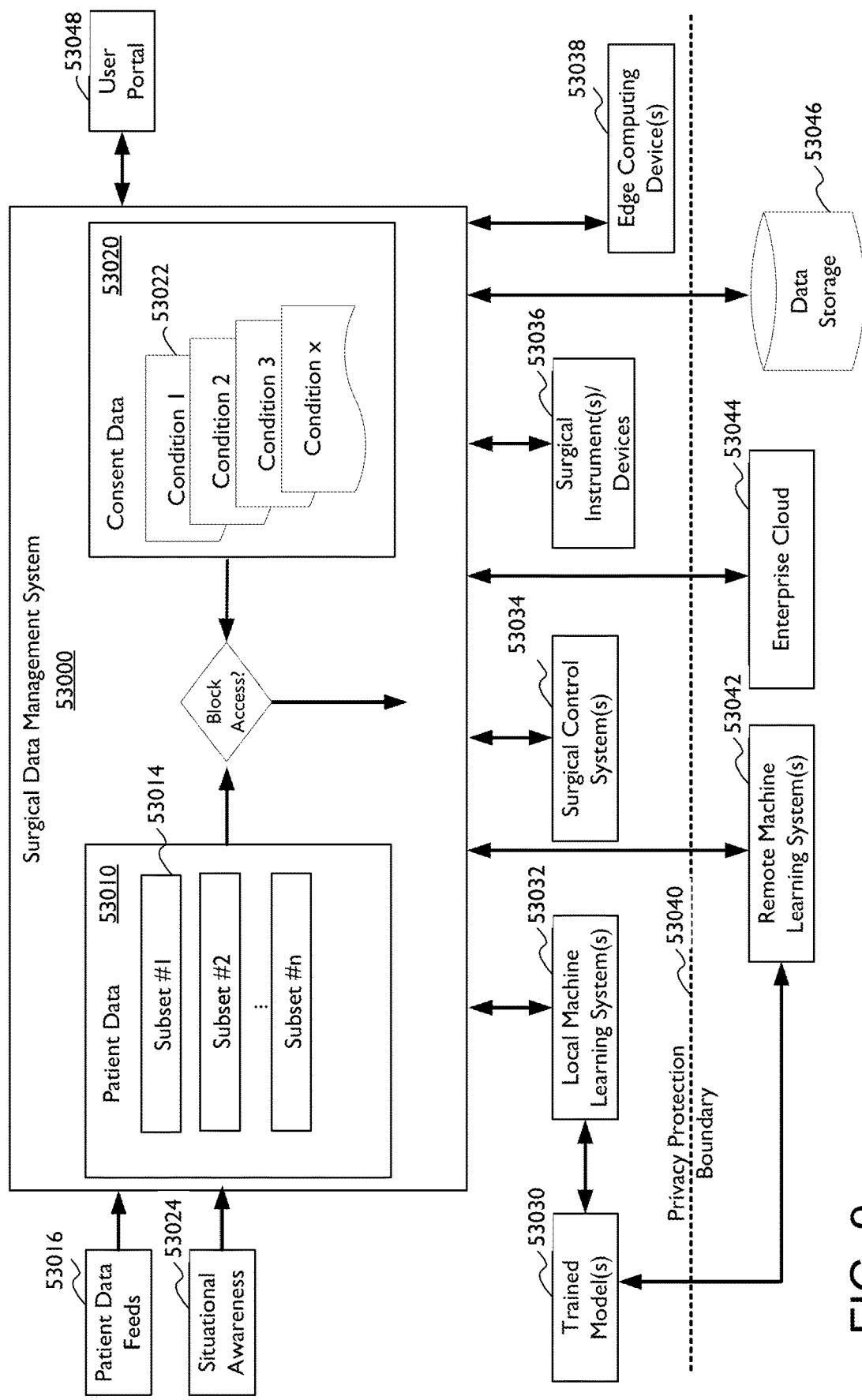
FIG. 9 shows an example surgical data management system with conditional patient consents.

FIG. 9 shows an example surgical data management system 53000 that may enable patients to provide consents. The surgical data management system may be or may include the surgical data system 45002 described herein with respect to FIG. 8. The surgical data management system 53000 may be part of a processor module of a surgical hub, for example, the processor module 20057 of the surgical hub 20006. The surgical data system 45002 may be a stand-alone system. While the surgical data management system 53000 is described in the context of managing surgical data, those skilled in art may appreciate that the techniques described herein apply to other managing other healthcare-related data.

As shown in FIG. 9, the surgical data management system 53000 may receive data from various patient data feeds 53016 and store patient data 53010. Patient data 53010 may include health data associated with various patients. Patient data 53010 may include the patient's electronic health record (EHR) within the privacy limits protected and controlled by HIPAA. For example, if the patient data includes patient-identifying information, HIPAA compliance protection of the data may be triggered. HIPAA may specify multiple rules, for example, Privacy Rule; Transactions and Code Sets Rule; Security Rule; Unique Identifiers Rule; Enforcement Rule. Most other major countries have similar laws, rules or requirements. Example patient-identifying information may include, but not limited to, names or part of names, information that may indicate unique identifying characteristic, geographical identifiers, dates directly related to a person, phone number details, fax number details, details of email addresses, social security details, medical record numbers, health insurance beneficiary numbers, account details, certificate or license numbers, vehicle license plate details, device identifiers and serial numbers, website URLs, IP address details, fingerprints, retinal and voice prints, complete face or any comparable photographic images, and/or the like. Health data may include personal data relating to the physical or mental health of an individual, including the provision of health care services, which reveals information about their health status. Health data may include data collected when a patient has an interaction with a health care provider (e.g., a primary physician, hospital or an organization, such as a universal health service.

Patient data feeds may include data feeds from one or more of environmental sensing system 20015, wearable sensing system 20011, human interface system 20012, robotic system 20013, intelligent instrument 20014, surgical system 20002, and/or the like as described herein with reference to FIGS. 1-4. The patient data feeds 53016 may include data feeds from human interface device 45014, surgical instrument(s) 45016, surgical hub(s) 45018, surgical data storage 45028, surgical data system 45002, and/or the like as described herein with reference to FIG. 8. Patient data 53010 may include data obtained from patients, their healthcare providers (e.g., data entered by the patient or their doctors), data generated by various systems, instruments and/or devices described herein, and/or data received from an external data source (e.g., patient data obtained from another healthcare provider). The patient data 53010 may include data generated by aggregating data feeds from the various data sources described herein. The patient data 53010 may include multiple subsets 53014. The subsets 53014 of patient data 53010 may be compartmentalized as described herein.

The surgical data management system 53000 may store patient consent data 53020. A healthcare provider may obtain permission or consent from patients to use and disclose their protected health data for treatment, payment, and health care operations. The use of a patient's electronic health data or medical records may be restricted based on the patient's consent. For example, only anonymized electronic medical records may be used. Personal identifying information may be either removed or blocked from access for the purpose of identifying patterns, improvements, and/or techniques that may be used to affect the operation of surgical tools for future use. A patient's consent may be associated with one or more conditions 53022 as described in detail herein.

The surgical data management system 53000 may provide a user interface (not shown) to allow patients to have direct control over the hierarchy of granted levels. The surgical data management system 53000 may monitor for triggering events that may trigger changes to a consent. Whether a triggering event has occurred may be determined based on situational awareness using situational awareness 53024 (e.g., as described herein with respect to FIG. 6). Examples of situation awareness may be disclosed in U.S. Patent Application Publication No. US 2019-0104919 A1 (U.S. patent application Ser. No. 16/209,478), titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE, filed Dec. 4, 2018, the disclosure of which is herein incorporated by reference in its entirety, and in U.S. Patent Application Publication No. US 2019-0206564 A1 (U.S. patent application Ser. No. 16/209,490), titled METHOD FOR FACILITY DATA COLLECTION AND INTERPRETATION, filed Dec. 4, 2018, the disclosure of which is herein incorporated by reference in its entirety, which, in one or more examples, describes where and/or how data is handled. Example data handling schemes are disclosed in U.S. patent application Ser. No. 17/384,348, titled SURGICAL DATA SYSTEM AND CLASSIFICATION, filed Jul. 23, 2021, the disclosure of which is herein incorporated by reference in its entirety.

The surgical data management system 53000 may monitor for triggering events that may trigger a verification of the consent. The surgical data management system 53000 may log, record, and catalog patient consents. Examples of secure consent recording and communications to HCPs are described in U.S. patent application Ser. No. 17/156,298, titled CONTEXTUAL TRANSFORMATION OF DATA INTO AGGREGATED DISPLAY FEEDS, filed Jan. 22, 2021, the disclosure of which is herein incorporated by reference in its entirety.

The surgical data management system 53000 may facilitate patient granting and revoking of consent for data logging and/or data usage. For example, the surgical data management system 53000 may record a patient's consent authorizing a healthcare provider's systems to collect and access the collected data. Various consent options may be presented to the patient, for example, via user portal 53048, and the patient consent data 53020 may be generated based on the patient's selection of the options.

The surgical data management system 53000 may provide a user interface to obtain a patient's consent for allowing certain type(s) of data collection. For example, the surgical data management system 53000 may present an option for the patient to indicate that data received directly from the patient (e.g., via the patient's data entry) can be collected. The surgical data management system 53000 may present an option for the patient to indicate that patient's data can or cannot be collected via surgical systems or surgical devices related to the surgical procedure for the patient. The surgical data management system 53000 may present an option for the patient to indicate that patient's data can or cannot be collected via various monitoring or sensing systems described herein with respect to FIG. 4.

The surgical data management system 53000 may provide a user interface to obtain a patient's consent for allowing the patient's medical records for certain specific use(s). For example, the surgical data management system 53000 may present an option for the patient to indicate that the patient's medical records and data collected can be only used for diagnosis of the patient. For example, the surgical data management system 53000 may present an option for the patient to indicate that the patient's medical records and data collected can be used to customize treatment of the patient. For example, the surgical data management system 53000 may present an option for the patient to indicate that the patient's medical records and data collected can be combined with other patient's data and can be used to enhance surgical control. The surgical data management system 53000 may present an option for the patient to indicate that the patient's medical records and other data collected can be accessed by certain systems, organizations, and/or facilities. For example, in U.S. Patent Application Publication No. US 2019-0206562 A1 (U.S. patent application Ser. No. 16/209, 416), titled METHOD OF HUB COMMUNICATION, PROCESSING, DISPLAY, AND COULD ANALYTICS, filed Dec. 4, 2018, the disclosure of which is herein incorporated by reference in its entirety, patient data may be used with smart interconnected systems to define the relationship(s) of the interconnected systems, cooperative behavior(s) of the interconnected systems, or monitoring and storage of procedure details, or the patient data may be aggregated to develop better algorithms, trends, or procedure adaption based on the comparison of the outcomes with the choices made in the procedures disclosed same application. Examples of data analytics are described in U.S. Pat. No. 10,966,791 B2 (U.S. patent application Ser. No. 15/940,694), titled CLOUD-BASED MEDICAL ANALYTICS FOR MEDICAL FACILITY SEGMENTED INDIVIDUALIZATION OF INSTRUMENT FUNCTION, filed Mar. 29, 2018, the disclosure of which is herein incorporated by reference in its entirety.

The surgical data management system 53000 may reconcile conflicting usage of or access to the data. The surgical data management system 53000 may receive a user indication to revoke the patient's consent. In response to the indication to revoke consent, the surgical data management system 53000 may remove data previously collected based on the consent revocation. The surgical data management system 53000 may instruct inter-related systems and/or devices to refrain from collecting data associated with the patient. The surgical data management system 53000 may instruct inter-related systems and/or devices to remove data associated with the patient based on the consent revocation. The surgical data management system 53000 may generate and present a validation or conformation notification to the patient that the associated instances of their data have been removed as requested.

The surgical data management system 53000 may log medical power of attorneys and/or other legal transfers of power to consent. Legal transfers of power to consent can be used to grant others the ability to access, transfer, consent, or revoke consent. This could be in addition to or in replacement of the patient's rights. For example, a patient may not necessarily have or need the legal right to consent or revoke consent. In these circumstances, a secondary server, security keys, or access granting or confirming could be on a separate key, system, server, etc. that would be needed in cooperation to the system holding or accessing the data in order to gain access and control aspects of the data.

The surgical data management system 53000 may securely record and store patient consent data 53020. For example, a patient's consent record(s) may be associated with an identifier of the person granting consent or a proxy for the consent. The consent may include a reference element that could be used to link the consent to the data without identifying the person who granted the consent or the person the data originated from. The person granting consent may be authenticated, and the consenter's authority to grant consent may be verified by the surgical data management system 53000. The surgical data management system 53000 may verify the consenter's cognitive ability to grant consent, as described herein. The surgical data management system 53000 may verify the consenter's legal authority to grant the consent. The surgical data management system 53000 may prompt the consenter to verify that the consenter understands the level and magnitude of the consent, their options for limiting the scope of the consent, and to verify their understanding of the consent. The consent may be associated with the data in the form of a key, encryption aspect, metadata, etc. The consent data 53020 may be stored with the protected patient data 53010 (e.g., to ensure proper handling of the patient's private data).

The surgical data management system 53000 may catalog patient consents. For example, the surgical data management system 53000 may provide a user portal 53048, which may be accessed by patients at facilities, networks, and/or treatment sites. The user portal 53048 may allow patients to catalog and review the consents they have given. For example, cataloging may be temporally based on a listing of the consents in a hierarchal order. Parent-child consent relationships could be displayed, allowing the patient to know who and how the consent was granted. Historical consent trees may be generated and presented. For example, a historical consent tree may be configured to depict how the initial consent to a specific facility or location has been expanded through that facility's relationships with other facilities or companies.

The surgical data management system 53000 may grant or block access to patient data 53010 based on the associated patient consent data 53020. For example, the surgical data management system 53000 may send patient data 53010 to various systems such as local machine learning system(s) 53032, surgical control system(s) 53034, surgical instrument(s)/device(s) 53036 (e.g., the surgical instrument(s) 45016 in FIG. 8), edge computing device(s) 53038, remote machine learning system(s) 53042, a cloud-based system in the enterprise cloud 53044 and/or a remote data storage 53046 (e.g., the surgical data storage 45028 in FIG. 8). Sending patient data may be in response to a data request from a data requesting system, in response to a triggering event, and/or based on a predetermined schedule (e.g., patient data may be sent periodically). Model(s) 53030 may be trained, for example, by the local machine learning system(s) 53032 and/or the remote machine learning system(s) 53042.

Examples of applying machine learning to a data collection to improve a surgical outcome are described in U.S. Patent Application Publication No. US 2022-0238216 A1 (U.S. patent application Ser. No. 17/156,293), titled MACHINE LEARNING TO IMPROVE ARTIFICIAL INTELLIGENCE ALGORITHM ITERATIONS, filed Jan. 22, 2021, the disclosure of which is herein incorporated by reference in its entirety. Details on utilizing health data to define one or more of the power, force, functional operation or behavior of a smart hand-held staple can be found in U.S. Pat. No. 10,881,399 B2 (U.S. patent application Ser. No. 15/628,175), titled TECHNIQUES FOR ADAPTIVE CONTROL OF MOTOR VELOCITY OF A SURGICAL STAPLING AND CUTTING INSTRUMENT, filed Jun. 20, 2017, the disclosure of which is herein incorporated by reference in its entirety. The collected dataset(s) may be used for comparisons to identify a configuration for the specific patient's needs (e.g., the most appropriate configuration(s) for the specific patient's needs), as disclosed in U.S. Patent Application Publication No. US 2020-0405296 A1 (U.S. patent application Ser. No. 16/458,103), titled PACKAGING FOR A REPLACEABLE COMPONENT OF A SURGICAL STAPLING SYSTEM, filed Jun. 30, 2019, the disclosure of which is herein incorporated by reference in its entirety.

For example, smart tools (e.g., robot(s) or laparoscopic device(s)) may use the health data to limit or minimize one or more of over-compression, collateral damage, or tissue tension, and/or to optimize usage location(s) and behavior(s), as described in U.S. Patent Application Publication No. US 2018-0049822 A1 (U.S. patent application Ser. No. 15/237,753), titled Control of advancement rate and application force based on measured forces, filed Aug. 16, 2016, the disclosure of which is herein incorporated by reference in its entirety.

For example, health data may be used to provide a situational awareness of the tissue and the surgical jobs and direct energy device(s) to adapt function or behavior resulting in improved outcomes, as disclosed in Ser. No. 16/209,458, filed Dec. 4, 2018, titled METHOD FOR SMART ENERGY DEVICE INFRASTRUCTURE, which is herein incorporated by reference in its entirety.

For example, health data may be used to enable robot(s) and advanced energy generator(s) to operate cooperatively to minimize unwanted side effects (e.g., tissue sticking) while improving tissue welding, as disclosed in in U.S. Patent Application Publication No. US 2019-0059929 A1 (U.S. patent application Ser. No. 15/689,072), titled Methods, systems, and devices for controlling electrosurgical tools, filed Aug. 29, 2017, the disclosure of which is herein incorporated by reference in its entirety.

For example, health data may be used with smart interconnected systems to define their relationship, cooperative behavior, monitoring and/or storage of procedure details. Health data could be aggregated for generation of algorithms, trends, or procedure adaption based on the comparison of the outcomes with the choices made in the procedures, for example as disclosed in, U.S. patent application Ser. No. 16/209,416, filed Dec. 4, 2018, entitled METHOD OF HUB COMMUNICATION, PROCESSING, DISPLAY, AND CLOUD ANALYTICS. Health data may be used for situational awareness, as disclosed in Ser. No. 16/209,478, filed, Dec. 4, 2018, entitled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE. Health data may be handled as disclosed in in U.S. Patent Application Publication No. US 2019-0206564 A1 (U.S. patent application Ser. No. 16/209,490), titled METHOD FOR FACILITY DATA COLLECTION AND INTERPRETATION, filed Dec. 4, 2018, the disclosure of which is herein incorporated by reference in its entirety.

For example, health data may be used to select a type of control program based on an operational mode of a device. Example of operational modes are described in U.S. Patent Application Publication No. US 2017-0202605 A1 (U.S. patent application Ser. No. 15/382,515), titled MODULAR BATTERY POWERED HANDHELD SURGICAL INSTRUMENT AND METHODS THEREFOR, filed Dec. 16, 2016, the disclosure of which is herein incorporated by reference in its entirety. A device equipped with a combination of energy devices may have the capability of utilizing more than one energy modalities and may use the energy modalities cooperatively or sequentially. Data collected from monitoring a patient (and potentially received from a smart hub system such as the surgical hub in FIG. 3) may provide the device the capacity of determining which operational mode is potentially more or the most useful.

Health data, including private data, public data, and population data and individual identifying data may be collected, stored and utilized for short term and/or long term, locally and/or remotely. The application of patient consents (e.g., conditional consents), regional-based privacy protection rules, and/or the like, may control and limit the collection, storage and/or utilization of health data.

As shown, some data requesting systems, such as local machine learning system(s) 53032, surgical control system(s) 53034, surgical instrument(s)/device(s) 53036 and edge computing device(s) 53038 may be located within the privacy protection boundary 53040. Some data requesting systems such as remote machine learning system(s) 53042, a cloud-based system in the enterprise cloud 53044 and/or a remote data storage 53046 may be located outside of the privacy protection boundary 53040. The privacy protection boundary 53040 may be the boundary of a network of an organization that collects the patient's data for diagnosis, treatment, billing, etc. The privacy protection boundary 53040 may be a HIPAA boundary.

The surgical data management system 53000 may enable a patient to provide conditional consent(s). The patient granted consent may be associated with one or more condition(s), stipulation(s), and/or limitations 53022 of the scope, duration, and/or usage of their health data. The surgical data management system 53000 may be configured to check that patient data 53010 is only being used in accordance with the consent data 53020 (e.g., for the agreed upon purpose(s) and for the agreed upon time, as discussed herein).

For example, based on the HIPAA rules described herein and/or other regional patient privacy protection rules, patient consent may be managed. Patient consents may be controlled by active granting of consent by a patient. A patient consent may specify (e.g., be associated with) consent for data collection, for specific purpose(s), and limits to the extents the collected data can be used, the duration for the collected data can be kept, the manner in which the collected data must be stored and protected, and/or the use of data to identify a specific individual out of a group of.

Consent may or may not be a durable agreement. The patient can alter what they have granted consent for and request a summary of where their data has been used, where their data is currently being held, and the limits of its use. These alterations can increase or decrease or even fully remove their data from being stored or used.

Figure 10:
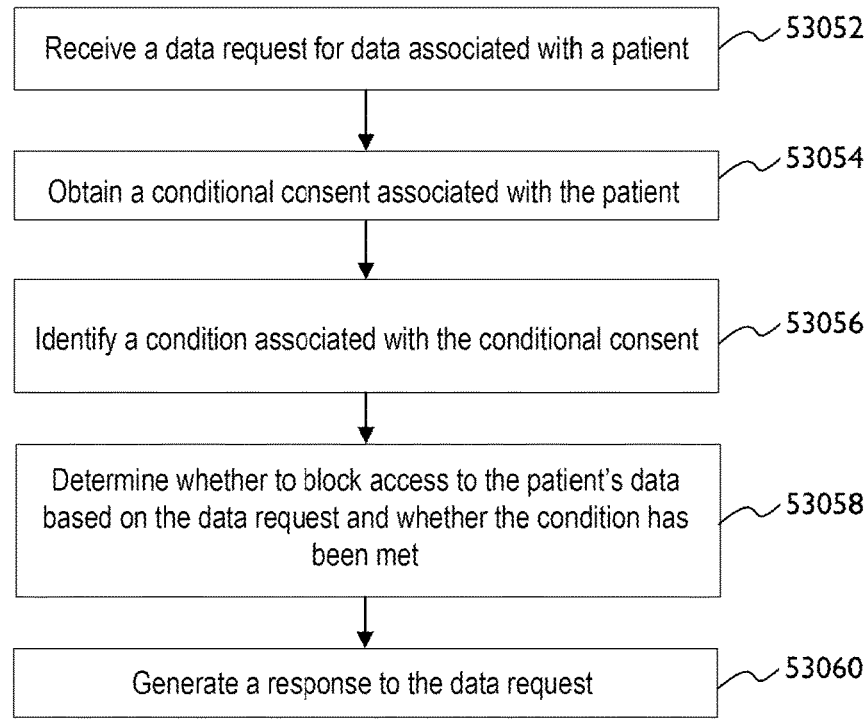
FIG. 10 shows an example process for patient data utilization control with conditional consents.

FIG. 10 shows an example patient data utilization control with conditional consents. As shown, at 53052, a data request associated with a patient may be received. The data request may be received from a data requesting system, such as local machine learning system(s) 53032, surgical control system(s) 53034, surgical instrument(s)/device(s) 53036, edge computing device(s) 53038, remote machine learning system(s) 53042, a cloud-based system in the enterprise cloud 53044 and/or a remote data storage 53046 shown in FIG. 8.

Referring back to FIG. 10, at 53054, a conditional consent associated with the patient may be obtained. The conditional consent may be obtained from the consent data 53020. As described herein, a conditional consent may be associated with one or more conditions, in accordance with a patient's selection when providing consent. At 53056, one or more conditions associated with the patient's consent may be identified. The conditions may be identified based on consent data 53020 shown in FIG. 8. The conditions may include two or more of the following, using the health data for diagnosis or treatment of the patient; using the health data with other patient health records for enhancing surgical control; limiting access to the health data to within a privacy protection boundary; limiting access to the health data to sharable health data; limiting access to the health data unless the patient lacks an ability to communicate; limiting access to the health data unless patient identifying data has been removed; and/or limiting access to the health data unless a threshold number of datasets similar to the requested health data have been accumulated. At 53058, whether to block access to the patient's data may be determined based on the data request and whether the condition has been met. At 53060, a response to the data request may be generated based on the determination. For example, upon determining that the condition has been met, the surgical data management system 53000 may activate the consent and include the requested patient data in the response. For example, upon determining that the condition has not been met, the surgical data management system 53000 may hold the patient's data in a protected state and may generate a response configured to block access to the health data associated with the patient.

For example, the surgical data management system 53000 may provide a user interface (e.g., via the user portal 53048 shown in FIG. 8) to obtain a patient's selection of duration of the consent. For example, the surgical data management system 53000 may present an option for a time-based consent. A time-based consent may expire after a predetermined time. A time-based consent may be associated with a specific start time and/or a specific end time. A time-based consent may not grant permission to collect and/or access data until a predefined time has elapsed. A time-based consent may be associated with one or more triggering events. For example, a first triggering event may activate a consent, and a second triggering event may deactivate a consent. The surgical data management system 53000 may hold the patient's data in a protected state (e.g., block access to the patient health data) until detecting the first triggering event, and may place the patient's data back in the protected state upon detecting the second triggering event. The triggering event may be a patient's clinical condition, e.g., loss of consciousness, loss of ability to communicate, etc. The triggering event may be the beginning and/or the ending of diagnosis, the beginning and/or the ending of treatment, the beginning and/or the ending of an operation, etc. The surgical data management system 53000 may activate the consent and release the patient's data that is usable locally for diagnosis or operation of treatment equipment. Upon detecting that the treatment is complete, the surgical data management system 53000 may hold the patient's data in a protected state. For example, the control programs of the surgical instrument(s)/devices 53036 may be returned to the default operation, where using and/or releasing patient specific data is blocked.

The surgical data management system 53000 may associate a conditional consent with one or more default aspects. A default aspect may be used in situations that exceed the specifically defined circumstances. For example, the default may be used to control data collection and/or data access when the patient's capacity to respond, adapt, or adjust the consent is in question.

The surgical data management system 53000 may associate a conditional consent with one or more limitations. In examples, a condition may include a limitation. For example, whether to activate a patient's consent may be determined based on a minimum number of data points requirement. Requiring a minimum number of data points in the data set for granting access to patient data may enable a patient to control when their data may be used. This may prevent their data from identifying them individually out of a group, thus balancing useful data analysis with privacy issues. The surgical data management system 53000 may hold the private patient data 53010 in a protected state (e.g., block access to the patient health data) based on the number of similar datasets in the system and the minimum number of data points requirement associated with the patient's consent. The surgical data management system 53000 may block access to the patient health data until a number of similar datasets have accumulated. The combined datasets could be shared together, masking the ability of anyone outside of the protected network to be able to use the data to identify a specific patient or user out of the combined set.

The magnitude of the needed data points may be determined. For example, the surgical data management system 53000 may determine the minimum number of needed datasets based on the uniqueness of the data combination being shared. The more unique the data point of a specific user, the more additional data points may be needed to be combined before sharing the data.

Figure 11:
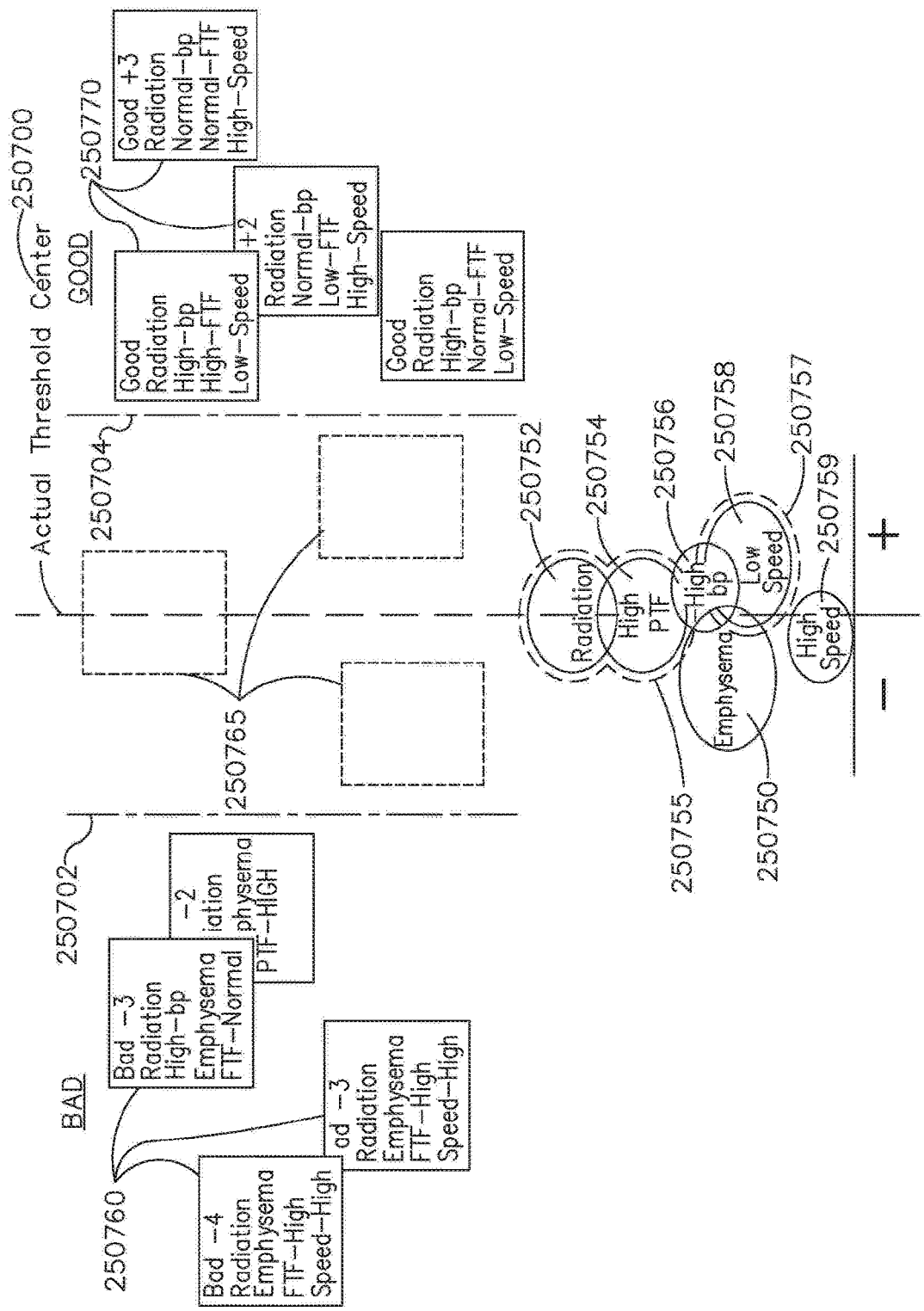
FIG. 11 shows an example surgical procedures having various characteristics grouped according to outcomes.
Figure 13:
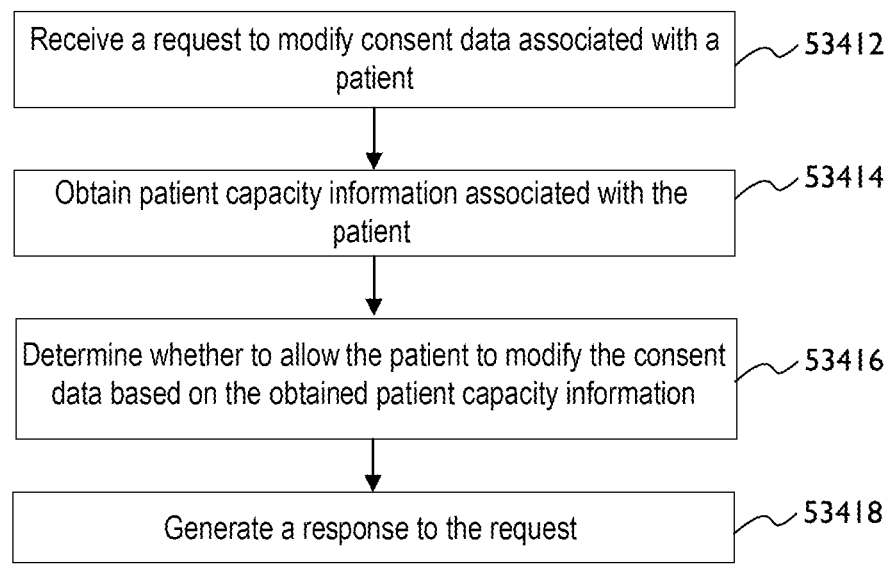
FIG. 13 shows an example process for consent management with capacity determination.

FIG. 11 shows example surgical procedures grouped into similar datasets. Machine learning can be utilized to identify interrelated causes and effects in the data, which can then be utilized to autonomously develop control program updates for the surgical instruments, surgical hubs, and/or other modular devices. As shown in FIG. 11, health data may be collected with respect to numerous parameters, including, for example: the stage of emphysema 250750; if the patient has received radiation 250752; the force required for a surgical stapler to advance its firing member 250754; the patient's blood pressure 250756; advancing the firing member at a low speed 250758; and/or advancing the firing member at a high speed 250759. As represented by the position of the measured parameters along the threshold line 250700, a parameter may a positive or negative effect on an outcome of a surgical procedure. As represented by the dashed line 250755, the patient having received radiation 250752 and the force required for a surgical stapler to advance its firing member 250754 being high both have an inter-related cause and effect on the outcome of the surgical procedure. High blood pressure 250756 and a low speed of advancement of a firing member 250758 have positive effects on the outcome of the surgical procedure, while a high speed of advancement of a firing member 250759 and a greater stage of emphysema 250750 have negative effects on the outcome of the surgical procedure. Dashed line 250757 represents a surgical instrument control program change based on unlearned grouping. Boxes 250760 represent measured parameters detected from individual patients whose combination resulted in a bad, or detrimental, outcome to the surgical procedure. Boxes 250770 represent measured parameters detected from individual patients whose combination resulted in a good, or beneficial, outcome to the surgical procedure. Boxes 250765 represent measured parameters detected from individual patients whose combination resulted in unexpected results that are not representative of other patients. In various instances, extenuating circumstances affected the result of the surgical procedure for the patients represented by 250765.

For example, the surgical data management system 53000 may receive a request to access patient health data related to a procedure in boxes 250760. The surgical data management system 53000 may determine whether to block access to the patient health data based on the number of datasets in boxes 250760. The surgical data management system 53000 may block access until a number of similar datasets have been accumulated in boxes 250760.

In an illustrative example, the surgical data management system 53000 may provide a patient an option to grant consent to use their general biometrics data, with a condition to limit the use of their co-morbidities, complications, or treatments to only being used within a dataset over a predefined number. For example, the surgical data management system 53000 may associate the patient's consent to use identifiable aspects like diabetes, high blood pressure, etc. with a minimum number of 10 similar data points. The surgical data management system 53000 may associate the patient's consent to use data related to morbidities of diabetes complication of vascular restrictions to the extremities with a higher number of minimum similar data points, such as 100 similar data points. Co-morbidities of diabetes complication of vascular restrictions to the extremities may be much easier to identify a specific person from, as the combination may be much less prevalent than diabetes or high blood pressure.

The minimum number of data points may be adjusted based on one or more mitigating operations. For example, surgical data management system 53000 may reduce the minimum number of needed data points by redacting certain portions of the dataset, or unlinking of identified co-morbidities (e.g., sharing averages not linked interrelationships of the patient complications).

The surgical data management system 53000 may associate a conditional consent with one or more circumstantial conditions. For example, the surgical data management system 53000 may hold the private data in a protected state (e.g., block access to the patient health data) until occurrence of certain circumstance(s). The surgical data management system 53000 may associate a conditional consent with whether the patient lacks the ability to speak or communicate. The surgical data management system 53000 may obtain patient monitoring data, for example, via the surgical system 20002 described herein with respect to FIG. 2. The surgical data management system 53000 may determine whether the patient monitoring data indicates the patient lacks the ability to communicate. For example, a patient may be considered lacking the ability to communicate when the patient is intubated for ventilation. Based on a determination that the patient lacks the ability to communicate, the surgical data management system 53000 may activate the consent and release the patient's data. The surgical data management system 53000 may put the patient's data in a protected state (e.g., block access to the patient health data) again, upon determining that the patient has regained the ability to communicate (e.g., based on patient monitoring data).

The surgical data management system 53000 may associate a conditional consent with conditions such as predefined clinical or treatment situation(s). For example, the customization of an orthopedics implant or the interpretation of a tumor scan may initiate the need for the patient's data to be uploaded to a remote server (e.g., a cloud server in the enterprise cloud 53044, or a remote machine learning system 53042). The upload may enable the remote server to generate a customized treatment for the patient based on the uploaded patient data. For example, the remote machine learning system 53042 may feed the uploaded patient data into a machine learning-trained model and send the customized treatment for the patient to the surgical data management system 53000 (and/or another system in the patient's protected network). The uploaded patient data may be combined with other datasets to identify the precise manner in which to size, place, or coordinate the images and models. In an example, the data may be uploaded for generating the specific customized treatment for the patient and may be removed from the remote server upon completion. In some examples, the uploaded patient data may be used for the customization and, at least a portion of the patient data may be added to the machine learning system 53042, for training the machine learning model to further customize other opportunities later for other patients as well.

The surgical data management system 53000 may associate a conditional consent with a subset of the patient's health data. For example, as shown in FIG. 8, patient data 53010 may include multiple subsets 53014. For example, a consent condition associated with a subset of the patient's data may allow a requester to use the data for a predefined purpose. The surgical data management system 53000 may determine whether to block access to the patient's data based on whether the requested data is to be used for a purpose and whether the requested data belongs to the subset of the patient's data that may be accessed for that purpose.

For example, the surgical data management system 53000 may associate access to a subset of the patient's data with diagnosis or treatment of the patient. If a data request indicates that the requested data is to be used for diagnosis or treatment of the patient, and the requested data fall within the subset of the patient's data releasable for diagnosis or treatment of the patient, the surgical data management system 53000 may grant access to the requested data. If a data request indicates that the requested data is to be used for diagnosis or treatment of the patient, and the requested data fall outside of the subset of the patient's data releasable for diagnosis or treatment of the patient, the surgical data management system 53000 may block access to the requested data. For example, the surgical data management system 53000 may associate access to a first subset of the patient's data with diagnosis or treatment of the patient and associate access to a second subset of the patient's data with enhancing surgical control. If a data request indicates that the requested data is to be used for enhancing surgical control (for example, for improving surgical control algorithms at various surgical devices), the surgical data management system 53000 may grant or deny the data request based on whether the requested data falls within the second subset of the patient's data.

Details on using health data associated with a patient to analyze and/or improve surgical device algorithmic behavior(s) can be found in U.S. Patent Application Publication No. US 2019-0200981 A1 (U.S. patent application Ser. No. 16/209,423), titled METHOD OF COMPRESSING TISSUE WITHIN A STAPLING DEVICE AND SIMULTANEOUSLY DISPLAYING THE LOCATION OF THE TISSUE WITHIN THE JAWS, filed Dec. 4, 2018, the disclosure of which is herein incorporated by reference in its entirety. For example, the control program of staplers may be generated (e.g., adapted, improved) based on the health data for one or more of better adaptation of the compression, speed of operation, and/or location of use. Health data may provide feedback for a specific use of a surgical instrument on a specific patient's tissue for a specific treatment disclosed. Example of data that may be used to train the machine learning model are described in U.S. patent application Ser. No. 17/449,765, titled COOPERATIVE ACCESS HYBRID PROCEDURES, filed Oct. 1, 2021, the disclosure of which is herein incorporated by reference in its entirety, in U.S. patent application Ser. No. 17/493,904, titled SURGICAL METHODS USING MULTI-SOURCE IMAGING, filed Oct. 1, 2021, the disclosure of which is herein incorporated by reference in its entirety, in U.S. patent application Ser. No. 17/493,913, titled SURGICAL METHODS USING FIDUCIAL IDENTIFICATION AND TRACKING, filed Oct. 5, 2021, the disclosure of which is herein incorporated by reference in its entirety, and in U.S. Patent Application Publication No. US 2020-0015907 A1 (U.S. patent application Ser. No. 16/128,195), titled INTEGRATION OF IMAGING DATA, filed Sep. 11, 2018, the disclosure of which is herein incorporated by reference in its entirety.

In some examples, the surgical data management system 53000 may remove patient identifying data from the patient's health data when sending the requested data. Examples of removing patient identifying data is described in Patent Application Publication No. US 2019-0201115 A1 (U.S. patent application Ser. No. 15/940,668), titled AGGREGATION AND REPORTING OF SURGICAL HUB DATA, filed Mar. 29, 2018, the disclosure of which is herein incorporated by reference in its entirety. As described in FIG. 28A of U.S. patent application Ser. No. 15/940,668, portion of the patient data may be removed, leaving anonymized, stripped patient data related to the patient's condition and/or the surgical procedure to be performed in the data set. A subset of patient data is removed to maintain patient anonymity for the processing of the data (including if the data is uploaded to the cloud for processing and/or data tracking for reports). The stripped patient data can include any medical conditions that the patient is suffering from, the patient's medical history (including previous treatments or procedures), medication that the patient is taking, and other such medically relevant details.

The surgical data management system 53000 may limit access to the patient's health data to systems within a privacy protection boundary, such as the privacy protection boundary 53040 shown in FIG. 8. The surgical data management system 53000 may determine whether to block access to the patient's data based on a location of the data requesting system relative to the privacy protection boundary 53040 (e.g., based on where the requested data is to be used). Based on a determination that the data is to be used within the privacy protection boundary (e.g., the requesting system is located within the privacy protection boundary), the conditional consent may be activated, and the requested data may be released. If the data request indicates that data is to be used outside of the privacy protection boundary (e.g., the data requesting system is located outside of the privacy protection boundary), access to the requested data may be blocked.

In examples, a default condition may be to limit access to the patient's health data to within the privacy protection boundary. The default condition may be overridden by direct permission only. In an example, a default condition may be to allow access to the health data associated with the patient to systems beyond the privacy protection boundary, unless the consent explicitly imposes the condition to limit access to systems within the privacy protection boundary.

The patient's health data may be segmented into different subsets 53014. Different subsets 53014 of the patient data 53010 may be associated with different privacy protection boundary-related access limitations. For example, the surgical data management system 53000 may determine that a first subset of the patient data may be released to a local machine learning system 53032 based on the local machine learning system 53032 being located within the privacy protection boundary 53040. The local machine learning system 53032 may use the patient data generate a trained model 53030, which may be sent to a remote machine learning system 53042. The surgical data management system 53000 may determine that a second subset of the patient data is not associated with the privacy protection boundary limitation and may send the second subset of the patient data to the remote machine learning system 53042. In examples, the surgical data management system 53000 may associate access to a first subset of the patient's data with allowing systems within the protected network to use the first subset, and associate access to a second subset of the patient's data with allowing systems beyond the protected network to use the second subset.

Each subset 53014 of patient data 53010 may be compartmentalized. The relationship between datasets may be maintained within a compartment, but the relationship between datasets across compartments may be removed. Data compartmentalization may be used in conjunction with the minimum number of data points limitation. Interrelated access to the patient's data may be granted based on other mitigating aspects of the shared data. The more other data protection or data concealment aspects are in use, the more interrelationships of the compartments could be shared. In this way, at least some lower-level information may be accessible. As the patient datasets increase (e.g., as more consents are granted by patients), more of the overall dataset can be shared together.

In an illustrative example, a patient may grant consent to use their general biometrics data, with a condition to limit the use within a predefined time period, such as one year. Upon expiry of the predefined time period, the surgical data management system 53000 may remove the patient's data. Such conditional consents may enable the patient to help the advancement of medical understanding while limiting their exposure to privacy concerns. The time-based limit could be associated with a triggering event. For example, the surgical data management system 53000 may allow a patient to consent to use of patient data after five years of treatment. For example, the surgical data management system 53000 may allow a patient to consent to use of patient data after the patient's death or five years after the patient's death. Before the starting time of this predefined time period, the surgical data management system 53000 may block access to the patient's data for any cooperative use. In an illustrative example, the surgical data management system 53000 may block access to the patient's data outside of the predefined time period, and within the predefined time period, the surgical data management system 53000 may limit the use of the patient's data within the protected network where it was collected (e.g., preventing the data from being uploaded, combined in the cloud, or sent to an original equipment manufacturer (OEM) device manufacturer level until after the patient's death).

An example patient data display system may be configured to determine its location and adjust its patient data access and display capabilities based on the location, the data origin, and/or the patient geographic characteristics with respect to regional or jurisdictional boundaries. The characteristics and regional aspects may be coupled to patients granting consent for the access or sharing of their private health data. Securing, redaction, inclusion and/or exclusion of data may be performed based on a predefined consent that is based at least partially on the location of the patient, their treatment location, the storage location of the patient's health data and/or the location of the HCP accessing the data. In examples, the geographic impact on the consent may change based on at least two locations globally. In examples, the changes may impact the completeness, permission, usage, inclusion and/or exclusion of data criteria, or the data within a larger data access usage.

A system, application, or sub-system may track the location of the patient relative to a regional border and the location of the system relative to a regional border and determine a control mode based on the location(s) relative to the regional border. The control mode may be a surgical control mode associated with operations of a surgical instrument (e.g., the surgical instrument(s)/devices 53036). The control mode may be a data storage control associated with controlling whether and how to store patient data. The control mode may be a data use mode associated with controlling the usage of patient data (e.g., patient's private data, or data derived or generated based on patient's private data).

For example, the surgical data management system 53000 may be, may include, or may be operatively connected to a patient data display system that may adjust patient data access and display capabilities based on the location, the data origin, and/or the patient geographic characteristics. The patient data display system may be located within or outside of the privacy protection boundary 53040 shown in FIG. 8.

The patient data display system may identify a region of the patient or a controlling jurisdiction of the patient's data usage. The surgical data management system 53000 may determine a regional law's bearing on patient consent and may adapt consent management accordingly. The surgical data management system 53000 may adjust patients' granted consents and privacy disclosures based on the controlling local laws and rules governing the protection of the patient health data.

For example, in the United States, the HIPAA required the federal government to develop regulations for protecting the privacy of personal health information. The HIPAA privacy regulations, which are intended to protect patient privacy, inhibit research that requires widespread sharing and multi-purpose use of data on individual patients. A consent or waiver of authorization to use identifiable health information may be granted by patients. For example, under HIPAA, authorization may be given for a specific use of patient data.

Aside from the U.S. federal regulation, regional laws may impose additional patient consent requirements. The HIPAA Privacy Rule provides a federal floor of privacy protections for individuals' individually identifiable health information. State laws that are contrary to the Privacy Rule are preempted by the Federal requirements, unless the State law relates to the privacy of individually identifiable health information and provides greater privacy protections or privacy rights with respect to such information. Thus, States may impose additional requirements for informed consent, such as requiring additional information to be disclosed in order for informed consent to be legally effective.

In addition, foreign jurisdictions may regulate patient data use and sharing differently than the United States. For example, privacy law differs substantially between the United States and Europe, beginning in its underlying philosophy. Generally speaking, in the United States, privacy laws focus on redressing consumer harm and attempting to balance privacy with efficient commercial transactions and the public interest; whereas in the European Union, privacy is treated as a fundamental right that can take precedence over other interests. In European Union countries, patient identifiable information may encompass all information identifiable to a person. Further, treaties between nations may regulate patient data use and sharing.

Figure 12:
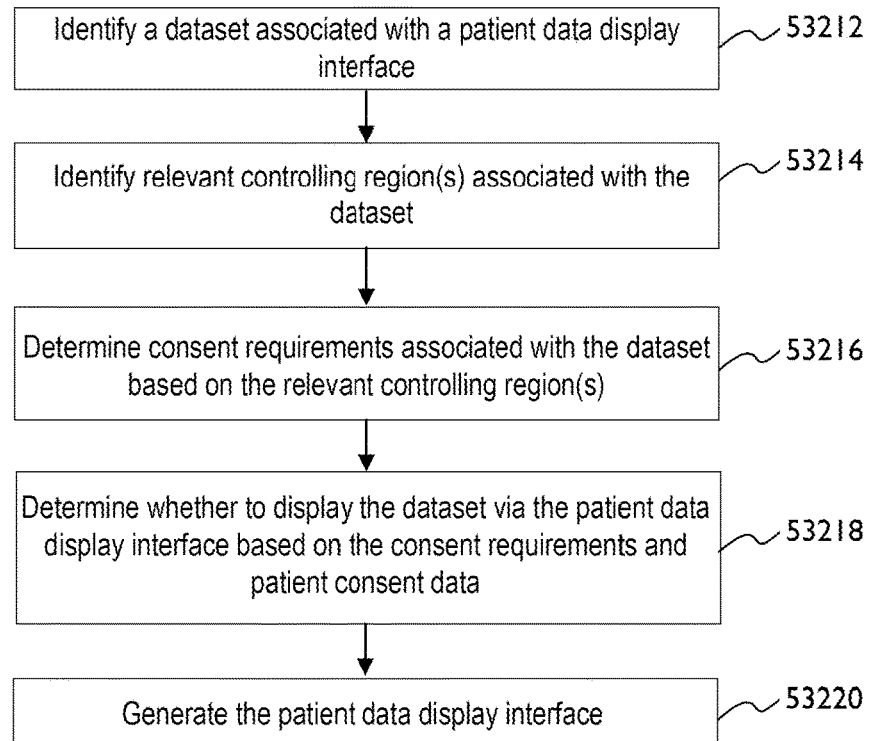
FIG. 12 shows an example process for patient data utilization control with region-based consent requirements.

FIG. 12 shows an example process for adjusting patient data access and display capabilities based on geographic region(s). For example, the patient data display system may be configured to generate a patient data display interface. The patient data display interface may be configured to display one or more datasets associated with one or more patients. The patient data display interface may be configured to perform other functions. At 53212, the dataset(s) associated with the patient data display interface may be identified. For example, a patient data display interface may be configured to obtain and display one or more datasets associated with one or more patients. Although FIG. 12 shows an example process for adjusting patient display capabilities based on geographic region(s), those skilled in art can readily appreciate that the process applies to adjusting system capabilities based on geographic region(s), adjusting patient data access capabilities based on geographic region(s), and/or adjusting patient data analysis capabilities based on geographic region(s) for the various patient data systems described herein, for example, with reference to FIG. 8.

At 53214, for a dataset associated with the patient data display interface, relevant controlling region(s) may be identified. The patient data display system may identify one or more regions/locations relevant to patient data privacy protection. Relevant controlling region type(s) may be identified, for example, based on the dataset. Examples of controlling region type(s) may include, but are not limited to, the geographic region associated with the patient data displaying system, the geographic region associated with the patient data origin, the geographic region associated with the patient location (e.g., primary residential location), the geographic region associated with patient treatment, the geographic region associated with the storage location of the patient data, the geographic region associated with a location associated with a health care provider accessing the patient data set via the patient data displaying system, and/or the like. For example, some jurisdictions could have rules around where the data was collected, and other jurisdictions may have rules around where data currently resides. Multiple relevant controlling regions and corresponding rules may be aggregated and/or synthesized to generate a comprehensive set of consent requirements.

In examples, whether certain datasets may be shared via the patient data display interface may be governed by a subset of controlling region type(s), whereas other datasets may be governed by a different subset of the controlling region type(s). For example, a first dataset associated with the patient data displaying system may be governed by the data storage location, and a second dataset may be governed by the patient's residential location. With the relevant controlling region type(s), the patient data display system may identify the relevant controlling regions associated with the dataset. For example, the region or jurisdiction in which the patient data display system is currently being used may be identified. The respective rules of consent and privacy management may be determined based on the region or jurisdiction in which the patient data display system is currently being used.

Systems, such as the patient data displaying system, may determine its location. The geographic location of a system may be determined based on a GPS system, a system key and/or a user interface. The geographic location of a system described herein (e.g., the one or more systems or devices shown in FIG. 8) may be determined based on an IP address, a domain name system identifier, a local system region designation, and/or the like. In an example, a patient data display system may determine its location and secure a connection to a server (e.g., a cloud server) to obtain regional-specific instructions and operational parameters.

At 53216, consent requirement(s) associated with the dataset may be determined based on the relevant controlling region(s). Based on the system's identification of geographic location, the patient data display system could adjust the consent needs to the local laws and requirements. The consent(s) required for accessing, sharing and/or displaying the dataset under the rules, laws and regulations in the relevant controlling region(s) may be determined. For example, certain datasets may be freely accessed in certain regions or jurisdictions without a patient's consent, while being protected in other regions or jurisdictions absent the patient's consent. In addition to local laws, facilities and/or networks may place their own local rules for consent and consent management. Consent requirement(s) associated with the dataset may be further determined based on the facilities and/or networks-imposed consent requirements.

For example, a surgical data display system may determine consent requirements via a lookup table. The look-up table may contain predetermined local and regional adaptation information and the surgical data display system may compare its location to that of the look-up table to determine its operational parameters. The operational parameters may indicate one or more of acceptable interactions, acceptable exchanges of information, acceptable operations of data processing, acceptable data storage, and/or the like. The operational parameters may indicate one or more of prohibited interactions, prohibited exchanges of information, prohibited operations of data processing, prohibited data storage, and/or the like, unless corresponding patient's consent(s) is obtained. In examples, the surgical data display system may maintain a primary set of rules that apply in various regions and operations and a secondary set of rules that may be applied based on facility, local, regional rules and/or agreements. The surgical data display system may present a user interface for a facility (e.g., a healthcare provider) to add their specific privacy rules and operations on top of the governmental rules of the region. This may enable a facility to be compliant with their detailed operational rules.

At 53218, whether to display the dataset via the patient data display interface may be determined based on the consent requirements associated with the dataset and the patient's consent data. As described herein, patient consent data may be captured and stored via the surgical data management system 53000. The consent requirements associated with the dataset may be compared against the patient consent data to determine whether proper consent has been obtained to display the dataset.

At 53220, the patient data display interface may be generated. Based on a determination to display a dataset (e.g., the region-based consent requirements have been met based on the patient's consent data), the patient data displaying system may display the dataset via the patient data display interface. In examples, the patient data display interface may be adjusted based on the relevant control region(s) and the patient's consent data. Adjustments may include, but are not limited to, adjustments to the data set(s) associated with the patient data display interface, enabling and/or disabling certain functions in the interface, and/or the like. Based on a determination to not display a dataset (e.g., the region-based consent requirements have not been met based on the patient's consent data), the patient data displaying system may exclude the dataset via the patient data display interface. The dataset may be redacted on the patient data display interface. The dataset may be omitted from the patient data display interface.

The patient portal 53048 may display the regional law and related impacts on the consent(s) granted. For example, some rules or laws may apply to a single jurisdiction. Some rules or laws may have multi-jurisdictional implications. The patient portal 53048 may display all the controlling or relevant rules for a patient, a patient's consent, and/or patient data based on the rules with single-jurisdiction effects and the rules with multi-jurisdictional effects. The patient portal 53048 may display expiring rules and/or the reasons why they are changing. Some rules may be universal and therefore apply in any locations and situations. Such universal rules may be highlighted differently.

Patient data 53010 may be adjusted based on the region associated with the data recipient. Patient data 53010 may be shared by facilities located in different parts of the world via the surgical data management system 53000. Language translation of data can modify the patient information and/or data. Patient data may be provided to the patient and/or the HCP accessing the data based on the regional languages, rules and/or customs. Language can be an important variable that can affect the exchange of information access to shared data. When words are translated and re-translated to other languages multiple times it can alter the output.

Patient data may be originated in one language and translated to a second language when accessed based on relevant region(s) associated with the patient data. The surgical data management system 53000 may prevent re-translation of patient data to maintain the integrity of the patient data. The system may determine whether to translate the patient data to or from a first language to a second language based on whether the first language is the language that the patient data originated in (e.g., base language). The system may impose a condition that the base language is the only file allowed to be used to convert to other languages. For example, if the original patient data is created in the U.S. then sent to China, when the patient data in Chinese is pulled to another country, the surgical data management system 53000 may prevent the patient data in Chinese from being translated into a third language. The surgical data management system 53000 may obtain the patient data in the base language and translate the surgical data management system 53000 to the third language.

Patient data 53010 may be converted from one unit of measurement to another based on relevant region(s) associated with the patient data. For example, some countries use imperial units, and some countries use metric units. When patient data is converted, the original value could alter based on the rounding limitations. The surgical data management system 53000 may use a base set of rules fixed within the system to minimize the errors (e.g., differences, rounding errors) during region-based data conversion. The surgical data management system 53000 may obtain the original data and the converted data and identify what the original data point was created for use within the algorithm.

In examples, the surgical data management system 53000 may be associated with multiple facilities (e.g., healthcare providers, medical treatment facilities, medical research facilities, etc.). A facility may use its own network. Patient data entered, collected, sensed and/or gathered in different facilities may be analyzed to generate information for diagnosing or treating a patient. In addition, patient data from different facilities may be used together for data projection, training machine learning models, medical research, and/or other purposes. For example, systems in different networks associated with different facilities may work together to generate a common material (procedural papers, journal articles, governmental reports, etc.). These facilities may be in independent but related or associated facilities. The facilities may obtain different consents from the same or different patients. For example, multiple separate facilities may have their own consent with the same patient. The surgical data management system 53000 may enable such facilities to pool patient consents such that handling of the patient data may be uniformly (e.g., consistently) controlled within exchanges among the systems associated with these facilities.

The surgical data management system 53000 may obtain patient consents (e.g., consents associated with a patient) from systems associated with multiple facilities. The surgical data management system 53000 may generate an aggregated patient consent (e.g., by aggregating, coupling, mingling, and/or reconciling the patient consent data from the different facilities). The aggregated patient consent may be used to control handling of the patient data. For example, whether to display the dataset via the patient data display interface may be determined based on the aggregated patient consent data.

The private data of a patient may be separated (e.g., bifurcated) into constituent parts. For example, private data of a patient may be separated based on the separation, disengagement, and/or breaking up of the related facilities associated with the surgical data management system. This may ensure that the patient data is only held or accessed by the portion holding the patient secured consent.

In examples, patient data that originated from a first facility may be shared with a second facility for diagnostic or treatment purposes. The second facility may store such patient data in its system. The surgical data management system 53000 may determine whether the patient data (e.g., a portion of the patient data) that originated from the first facility is to be removed from the system associated with the second facility. Such determination may be based on one or more trigger events, such as patient's modification or revocation of consent from the first facility, expiry of a consent, completion of treatment, transfer of patient, etc. For example, all or part of the patient data may be removed from the second facility based on a determination that the first facility, where the patient data originated from, is no longer treating or interacting with the patient. As described herein, a time-based consent may expire after a predetermined time. A patient's consent to data sharing among different facilities may expire, and the shared access and use of the data is terminated upon expiry of the consent. Based on a determination that the data sharing consent is expired, all or part of the patient data may be removed from the second facility. The data origination information may be generated, stored, and used as metadata. Data origination information may be used to determine whether one, none, or both of the facilities are allowed to retain and use the private patient data.

The surgical data management system 53000 may prompt an HCP to obtain a secondary consent from patients for an original equipment manufacturer (OEM) manufacturer to gather information for the improvement of a device or procedure. This consent could have special aspects from the original patients that would limit prolonged use or exchange of the information related to a pre-specified use. The data could be coupled to an element that may ensure the destruction of the data under these specific conditions or when the conditions have been met for the original sharing.

A patient must have the capacity to grant, revoke, and/or modify consent to use and access the patient's private health data (e.g., the patient data 53010) before the patient is allowed to make such modifications. Generally, a determination of capacity is performed by a health care provider, such as the patient's PCP. However, a patient may have limited access to a health care provider who can determine the patient's capacity. For example, the patient may live far away from the health care provider's office, the patient may have limited financial resources, and/or the patient may have mobility issues which make it difficult to visit a health care provider. Accordingly, a system that can determine a patient's capacity to modify consent data (e.g., the consent data 53020) may allow patients to modify their consent data without having to visit a health care provider for a capacity determination.

For example, as shown in FIG. 8, the user portal 53048 may include a patient capacity module 53050 for determining whether a patient has the capacity to grant, revoke, and/or modify consent data 53020. The patient capacity module 53050 may then convey the determination to the surgical data management system 53000. In some examples, the patient capacity module 53050 may determine if the patient has the capacity to add, remove, and/or modify one or more conditions 53022 in the consent data 53020. While the patient capacity module 53050 is illustrated as a part of the user portal 53048, those skilled in the art will appreciate that the patient capacity module 53050 may be a stand-alone system, part of the surgical data management system 53000, or part of both the surgical data management system 53000 and the user portal 53048.

FIG. 1 shows an example process for consent management with capacity determination. A consent management system, which includes the patient capacity module 53050, may be configured to make the capacity determination (e.g., determine whether the patient has capacity to modify the consent data 53020).

In some examples, the capacity determination may begin at 53412, with the consent management system receiving (e.g., via the user portal 53048) a request to modify consent data associated with a patient. The request may come from the patient or from a person with authority (e.g., power of attorney) to modify the consent data associated with the patient. In some examples, the consent management system may be configured to verify that the person making the request has the authority to make such a request. For example, the patient capacity module 53050 may include a digital interface configured to authenticate that the person attempting to modify the consent data has the authority to do so.

At 52414, the consent management system may obtain (e.g., via the patient capacity module 53050) patient capacity information associated with the patient. Obtaining the patient capacity information may include determining the patient's cognitive (e.g., mental) capacity. For example, the determination may include determining whether the patient is able to understand the nature and effects of the patient's decisions. For example, the determination of the patient's capacity may be based on detecting the occurrence of a consent modification triggering event. For example, event information may indicate that a medical power of attorney has been executed and is in force. As a result, the consent management system may determine that the patient no longer has the capacity to modify their consent data. The system may determine that only the person with the medical power of attorney is authorized to modify consent data.

The consent management system may determine patient capacity information using a capacity assessment module. The capacity assessment module may be internal or external to the consent management system. For example, the capacity assessment module may include a wearable device that may be configured to assess the state of mind of the user based on the patient's biomarker measurements (e.g., blood alcohol concentration, oxygen saturation, blood sugar, hydration state, blood pressure, heart rate, etc.). Details on a wearable device that may be used for consent recording, are described in U.S. patent application Ser. No. 17/156,298, titled CONTEXTUAL TRANSFORMATION OF DATA INTO AGGREGATED DISPLAY FEEDS, filed Jan. 22, 2021, the disclosure of which is herein incorporated by reference in its entirety. A state of mind of the user may be determined as described in U.S. patent application Ser. No. 17/156,298, and consent of the user may be confirmed based on the confirmation that the state of mind of the user indicates the user is able to provide the consent. The capacity assessment module may include a user interface configured to ask the patient a series of questions and assess capacity information based on the received answers.

In some examples, obtaining the patient capacity information may include determining the patient's emotional capacity. The consent management system may determine whether the patient is overwhelmed and/or experiencing emotions that are outside of normal emotions for a person to be able to understand and agree to or modify consent at that time. In some examples, the patient capacity information may be based, at least in part, on input(s) from another system. The consent management system may determine the patient's emotional capacity based on biomarker measurement(s) obtained via one or more sensing systems described herein, such as the wearable sensing system 20011, the environmental sensing system 20015, and/or the situational awareness system.

For example, the consent management system may determine the patient's emotional capacity based on biomarker measurement(s) obtained via a wearable sensing system 20011 described herein. The consent management system may determine the patient's emotional capacity based on measurement(s) associated with one or more biomarkers such as heart rate, heart rate variability body temperature, respiration rate, blood pressure, perspiration, and/or the like. Heart rate variability (HRV), a measure of the variability in intervals between subsequent heart beats, may be used to assess the patient's emotional capacity.

For example, the consent management system may determine the patient's emotional capacity based on the patient's environment, the way the patient is acting, and/or information provided to the patient. The consent management system may determine the patient's emotional capacity based on environmental information obtained via environmental sensing system(s) 20015 described herein. For example, the environmental information gathered via the environmental sensing system(s) 20015 may indicate that the patient is in a large group of people and may determine that the patient lacks the emotional capacity to grant, revoke or consent. For example, the environmental information gathered via the environmental sensing system(s) 20015 may indicate that the patient is in a very loud setting and may determine that the patient lacks the emotional capacity to grant, revoke or modify consent.

At 53416, the system may determine whether to allow the patient to modify the consent data based on the obtained patient capacity information. For example, whether to grant the patient access to adjust the consent data 53020 may be determined based on a cognitive analysis, emotional analysis, event monitoring, situational awareness, and/or a determination of capacity by an HCP. In some examples, the determination of capacity may be achieved by a system algorithm. The system may make the determination by comparing the patient capacity information to a value, such as a capacity threshold. For example, if the comparison indicates that the patient has greater capacity than the capacity threshold, then the system may allow the patient to modify the consent data. However, if the comparison indicates that the patient has less capacity than the capacity threshold, the system may be configured to block the patient from modifying the consent data.

As described herein, the consent data associated with the patient may include consent rules associated with access to the patient's health data. In some examples, the patient capacity information may include cognitive capacity information associated with the patient. The system may determine that the request to modify the consent data is associated with adjusting a consent rule. The system may identify the cognitive capacity threshold associated with (e.g., required for) changing the consent rule. The system may compare the cognitive capacity information associated with the patient to the identified cognitive capacity threshold. The system may determine whether the comparison of the cognitive capacity information to the cognitive capacity threshold indicates that the patient has cognitive capacity to adjust the consent rule. For example, if the cognitive capacity information associated with the patient is below the cognitive capacity threshold, then the consent management system may determine that the patient lacks cognitive capacity to modify the consent data and may deny the request to modify the consent data.

In some examples, the consent data associated with the patient may include consent rules and the patient capacity information may include emotional capacity information associated with the patient. The system may be configured to determine that the request to modify the consent data is associated with adjusting a consent rule of the plurality of consent rules associated with access to health data associated with the patient. The system may also be configured to compare the emotional capacity information associated with the patient to an emotional capacity threshold. The system may be configured to determine whether the comparison of the emotional capacity information associated with the patient to the emotional capacity threshold indicates that the patient has emotional capacity to adjust the consent rule. For example, if the emotional capacity information associated with the patient is below the emotional capacity threshold, then the consent management system may determine that the patient lacks emotional capacity to modify the consent data and may deny the request to modify the consent data.

The consent management system may determine whether to allow the patient to modify the consent data based on the consent modification type associated with the request. In some examples, the capacity threshold (e.g., the cognitive capacity threshold and/or the emotional capacity threshold) may be static. In some examples, the capacity threshold may vary depending on the type of modification to the consent data requested by the patient. For example, the consent management system may determine a consent modification type associated with the request. The system may obtain a capacity threshold associated with the determined consent modification type. The system may further compare the patient capacity information associated with the patient to a capacity threshold associated with the determined consent modification type. For example, the consent modification type may be at least one of: granting consent, revoking consent, adding a consent rule, removing a consent rule, and modifying a consent rule For example, if the patient is requesting to grant consent to a new HCP, then the capacity threshold may be higher than if the patient was requesting to revoke consent that was previously granted. For example, the capacity threshold may be lower if the patient is requesting to remove a condition from the conditions 53022 than if the patient is requesting to add a condition. For example, the capacity threshold may be higher if the patient is requesting to modify a condition so that the condition is less limiting than if the patient is requesting that the condition be more limiting.

The consent management system may monitor for triggering events that may trigger review of the patient by an HCP. Whether a triggering event has occurred may be determined based on situational awareness using situational awareness 53024 (e.g., as described herein with respect to FIG. 6). For example, the triggering event may include a change in the patient's capacity. For example, the consent management system may obtain surgical context information associated with the patient using situational awareness

53024, and obtain a requirement associated with the consent modification request based on the surgical context information. The consent management system may then determine, based on the requirement, whether an HCP review is required before generating the response. If the consent management system determines that the HCP review is required, the system may send an HCP review request to another system associated with the health care provider. For example, the system may determine that the patient was recently under general anesthesia. In this case, the system may determine that an HCP needs to determine that the effects of the anesthesia have subsided enough for the patient to have regained capacity to modify the consent data.

In some examples, the consent management system may perform event monitoring related to events outside of a surgical context. The system may make the capacity determination based on the event monitoring. The system may adjust the cognitive capacity threshold based on event information. For example, the consent management system may obtain event information associated with the patient and determine, based on the event information, whether the patient has capacity to modify the consent data. For example, event information may indicate that a medical power of attorney has been executed and is in force. As a result, the consent management system may determine that the patient no longer has the capacity to modify their consent data. The system may determine that only the person with the medical power of attorney is authorized to modify consent data. As another example, the system may determine that the patient consumed alcohol and is too inebriated to have capacity to modify the consent data (e.g., based on biomarker measurements obtained via a wearable sensing system described herein). As yet another example, the system may determine that the patient has begun a new treatment that may affect the patient's cognitive abilities. Accordingly, the system may raise the capacity threshold to ensure that the patient does not modify consent data while under the effects of the treatment.

At 53418, the system may then generate a response to the request. For examples, the response may be an indication that the request has been granted or denied. In some examples, the response may include additional information about why the request was granted or denied.

For example, the system may determine that the patient's capacity should be reviewed by an HCP (e.g., a psychiatrist or psychologist) and the response to the request may indicate that determination. The system may determine that the patient should be monitored over a period of time to allow the patient to confirm consent again or provide the patient with time to process the decision before reconfirming. For example, the system may determine that a preconfigured amount of time has lapsed after the receipt of a request from the patient. The system may generate a prompt for the patient to resubmit (e.g., reconfirm) the request to modify the consent data. In another example, the system receives a second request to modify the consent data from the patient. The system may determine how much time passed between the requests. The system may further determine whether to allow the patient to modify the consent data. The determination may be based on the amount of time. For example, if the patient submits an identical request immediately after the first request was denied, the system may deny the subsequent request without having to re-determine the patient's capacity.

In some examples, the system may receive a second request to modify the consent data from the patient. The system may determine whether an environment surrounding the patient has changed between reception of the first request and reception of the second request. The system may then generate a response to the second request based on the environment surrounding the patient. For example, if the patient is in a large group of people when the first request is made, then the first request may be denied. However, if the patient is alone when the second request is made, then the consent management system may determine to grant the second request because the change in the patient's environment suggests that the patient has higher emotional capacity to modify the consent data compared to when the patient was in a group of people.

In some examples, the system may determine that the patient's environment should be altered to allow the patient to better process their decision prior to modifying the consent data. For example, the system may determine that the patient is around a large group of people, so the system may decide to wait for the patient to be alone before allowing the patient to modify the consent data. This may prevent the patient from being unduly influenced by people in the group.

The patient capacity information and/or the capacity determination may be stored with metadata of the access data to create a documentation trail of the data from generation through complete usage. In some examples, the consent management system may use the patient's capacity information as at least a portion of the HCP's (or other user's) accessing credentials.

The invention claimed is:

1. A consent management system, comprising:
   a processor configured to:
      detect an occurrence of a consent modification triggering event associated with a patient;
      in response to detecting the occurrence of the consent modification triggering event, receive a request to modify consent data associated with the patient;
      determine a consent modification type associated with the request;
      determine a capacity threshold associated with the determined consent modification type;
      obtain patient capacity information associated with the patient;
      compare the patient capacity information associated with the patient to the capacity threshold associated with the determined consent modification type;
      allow modification of the consent data based on the obtained patient capacity information and the comparison;
      modify the consent data in accordance with the request; and
      update a training data set for a machine learning model based on the modified consent data and wherein training data includes segmented privacy protection boundaries.

2. The consent management system of claim 1, wherein the consent data associated with the patient comprises a plurality of consent rules, the patient capacity information comprises cognitive capacity information associated with the patient, and the processor is further configured to:
   determine that the request to modify the consent data is associated with adjusting a consent rule associated with access to health data associated with the patient;
   compare the cognitive capacity information associated with the patient to a cognitive capacity threshold; and determine whether the comparison of the cognitive capacity information to the cognitive capacity threshold indicates that the patient has cognitive capacity to adjust the consent rule.

3. The consent management system of claim 1, wherein the consent data associated with the patient comprises a plurality of consent rules, the patient capacity information comprises emotional capacity information associated with the patient, and the processor is further configured to:
determine that the request to modify the consent data is associated with adjusting a consent rule associated with access to health data associated with the patient;
compare the emotional capacity information associated with the patient to an emotional capacity threshold; and
determine whether the comparison of the emotional capacity information to the emotional capacity threshold indicates that the patient has emotional capacity to adjust the consent rule.

4. The consent management system of claim 1, wherein the consent data associated with the patient comprises a plurality of consent rules, and the consent modification type comprises at least one of: granting consent, revoking consent, adding a consent rule, removing a consent rule, or modifying a consent rule.

5. The consent management system of claim 1, wherein the processor is further configured to:
obtain surgical context information associated with the patient;
determine, based on the surgical context information and the request to modify the consent data, whether a health care provider review is required before generating the response; and
based on a determination that the health care provider review is required, generate a health care provider review request.

6. The consent management system of claim 1, wherein the processor is further configured to:
determine that a predetermined amount of time has lapsed after reception of the request; and
generate a prompt for the patient to resubmit the request to modify the consent data.

7. The consent management system of claim 1, wherein the request is a first request, and the processor is further configured to:
receive a second request to modify the consent data associated with the patient;
determine an amount of time between reception of the first request and reception of the second request; and
generate a response to the second request based at least in part on the amount of time.

8. The consent management system of claim 1, wherein the request is a first request, and the processor is further configured to:
receive a second request to control access to health data associated with the patient;
obtain surrounding environment information associated with the patient;
determine, based on the surrounding environment information, whether an environment surrounding the patient has changed between reception of the first request and reception of the second request; and
generate a response to the second request based at least in part on the environment surrounding the patient.

9. The consent management system of claim 1, wherein the processor is further configured to:
store the obtained capacity information associated with the patient as metadata of health data associated with the patient.

10. The consent management system of claim 1, wherein the determining is based, at least in part, on input from a system separate from the consent management system.

11. A method for consent management, the method comprising:
detecting an occurrence of a consent modification triggering event associated with a patient;
in response to detecting the occurrence of the consent modification triggering event, receiving a request to modify consent data associated with the patient;
determining a consent modification type associated with the request;
determining a capacity threshold associated with the determined consent modification type;
obtaining patient capacity information associated with the patient;
compare the patient capacity information associated with the patient to the capacity threshold associated with the determined consent modification type;
allowing modification of the consent data based on the obtained patient capacity information and the comparison;
modifying the consent data in accordance with the request; and
update a training data set for a machine learning model based on the modified consent data and wherein training data includes segmented privacy protection boundaries.

12. The method of claim 11, wherein the consent data associated with the patient comprises a plurality of consent rules, the patient capacity information comprises cognitive capacity information associated with the patient, the method further comprising:
determining that the request to modify the consent data is associated with adjusting a consent rule associated with access to health data associated with the patient;
comparing the cognitive capacity information associated with the patient to a cognitive capacity threshold; and
determining whether the comparison of the cognitive capacity information to the cognitive capacity threshold indicates that the patient has cognitive capacity to adjust the consent rule.

13. The method of claim 11, wherein the consent data associated with the patient comprises a plurality of consent rules, the patient capacity information comprises emotional capacity information associated with the patient, the method further comprising:
determining that the request to modify the consent data is associated with adjusting a consent rule associated with access to health data associated with the patient;
comparing the emotional capacity information associated with the patient to an emotional capacity threshold; and
determining whether the comparison of the emotional capacity information to the emotional capacity threshold indicates that the patient has emotional capacity to adjust the consent rule.

14. The method of claim 11, wherein the consent data associated with the patient comprises a plurality of consent rules, and the consent modification type comprises at least one of: granting consent, revoking consent, adding a consent rule, removing a consent rule, or modifying a consent rule.

15. The method of claim 11, further comprising:
obtaining surgical context information associated with the patient;

determining, based on the surgical context information and the request to modify the consent data, whether a health care provider review is required before generating the response; and based on a determination that the health care provider review is required, generating a health care provider review request.

16. The method of claim 11, further comprising:

determining that a predetermined amount of time has lapsed after the reception of the request; and generating a prompt for the patient to resubmit the request to modify the consent data.

17. The method of claim 11, wherein the request is a first request, the method further comprising:

receiving a second request to modify the consent data associated with the patient;

determining an amount of time between reception of the first request and reception of the second request; and generating a response to the second request based at least in part on the amount of time.

* * * * *